United States Patent
Bilic et al.

(10) Patent No.: US 11,078,191 B2
(45) Date of Patent: Aug. 3, 2021

(54) 1-(4-AMINO-5-BROMO-6-(1H-PYRAZOL-1-YL)PYRIMIDIN-2-YL)-1H-PYRAZOL-4-OL AND USE THEREOF IN THE TREATMENT OF CANCER

(71) Applicants: Novartis AG, Basel (CH); Palobiofarma S.L., Mataro Barcelona (ES)

(72) Inventors: Sanela Bilic, Urbandale, IA (US); Juan Alberto Camacho Gomez, Mataro Barcelona (ES); John Scott Cameron, Belmont, MA (US); Julio Cesar Castro-Palomino Laria, Matero Barcelona (ES); Danny Roland Howard, Jr., Washington, NJ (US)

(73) Assignees: Novartis AG, Basel (CH); Palobiofarma S.L., Barcelona (ES)

( * ) Notice: Subject to any disclaimer, the term of this patent is extended or adjusted under 35 U.S.C. 154(b) by 0 days.

(21) Appl. No.: 16/484,183

(22) PCT Filed: Feb. 8, 2018

(86) PCT No.: PCT/IB2018/050783
§ 371 (c)(1),
(2) Date: Aug. 7, 2019

(87) PCT Pub. No.: WO2018/146612
PCT Pub. Date: Aug. 16, 2018

(65) Prior Publication Data
US 2019/0359600 A1    Nov. 28, 2019

Related U.S. Application Data

(60) Provisional application No. 62/457,219, filed on Feb. 10, 2017.

(51) Int. Cl.
| | | |
|---|---|---|
| *C07D 403/14* | (2006.01) | |
| *C07K 16/28* | (2006.01) | |
| *A61K 31/506* | (2006.01) | |
| *A61P 35/00* | (2006.01) | |

(52) U.S. Cl.
CPC .......... *C07D 403/14* (2013.01); *A61K 31/506* (2013.01); *A61P 35/00* (2018.01); *C07K 16/2818* (2013.01); *C07K 16/2827* (2013.01); *C07K 2317/565* (2013.01)

(58) Field of Classification Search
CPC ...... C07D 403/14; A61K 31/506; A61P 35/00
See application file for complete search history.

(56) References Cited

U.S. PATENT DOCUMENTS 10,561,653 B2 *   2/2020   Bilic ................. C07K 16/2827

FOREIGN PATENT DOCUMENTS

| WO | 2007/005874 | 1/2007 |
| WO | 2009/114335 | 9/2009 |
| WO | WO2011/121418 A1 | 10/2011 |
| WO | 2014/209804 | 12/2014 |
| WO | WO2017/025918 A1 | 2/2017 |

* cited by examiner

*Primary Examiner* — Kevin E Weddington
(74) *Attorney, Agent, or Firm* — Michelle Han

(57) ABSTRACT

This invention relates to an active metabolite of 5-bromo-2,6-di(1H-pyrazol-1-yl)pyrimindin-4-amine that modulates the activity of adenosine A2a receptor. In particular, the present invention relates to pharmaceutical compositions comprising 1-(4-amino-5-bromo-6-(1H-pyrazol-1-yl)-pyrimidin-2-yl)-1H-pyrazol-4-ol, as well as processes for its preparation and its use in the treatment of cancer alone of in combination with one or more immunotherapeutic agents.

23 Claims, 4 Drawing Sheets
Specification includes a Sequence Listing.

SEQUENCE LISTING

```
<160> NUMBER OF SEQ ID NOS: 63

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Thr Tyr Trp Met His
1               5

<210> SEQ ID NO 2
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                    Synthetic peptide"

<400> SEQUENCE: 2

Asn Ile Tyr Pro Gly Thr Gly Gly Ser Asn Phe Asp Glu Lys Phe Lys
1               5                   10                  15

Asn

<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Trp Thr Thr Gly Thr Gly Ala Tyr
1               5

<210> SEQ ID NO 4
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Thr Phe Thr Thr Tyr
1               5

<210> SEQ ID NO 5
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Tyr Pro Gly Thr Gly Gly
1               5

<210> SEQ ID NO 6
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Thr Tyr
                20                  25                  30

Trp Met His Trp Val Arg Gln Ala Thr Gly Gln Gly Leu Glu Trp Met
            35                  40                  45

Gly Asn Ile Tyr Pro Gly Thr Gly Gly Ser Asn Phe Asp Glu Lys Phe
        50                  55                  60

Lys Asn Arg Val Thr Ile Thr Ala Asp Lys Ser Thr Ser Thr Ala Tyr
```

```
                 65                  70                  75                  80
Met Glu Leu Ser Ser Leu Arg Ser Glu Asp Thr Ala Val Tyr Tyr Cys
                         85                  90                  95

Thr Arg Trp Thr Thr Gly Thr Gly Ala Tyr Trp Gly Gln Gly Thr Thr
                100                 105                 110

Val Thr Val Ser Ser
        115
```

<210> SEQ ID NO 7
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

```
gaggtgcagc tggtgcagtc aggcgccgaa gtgaagaagc ccggcgagtc actgagaatt      60
agctgtaaag gttcaggcta caccttcact acctactgga tgcactgggt ccgccaggct     120
accggtcaag gcctcgagtg gatgggtaat atctaccccg gcaccggcgg ctctaacttc     180
gacgagaagt ttaagaatag agtgactatc accgccgata agtctactag caccgcctat     240
atggaactgt ctagcctgag atcagaggac accgccgtct actactgcac taggtggact     300
accggcacag gcgcctactg gggtcaaggc actaccgtga ccgtgtctag c              351
```

<210> SEQ ID NO 8
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

```
Glu Val Gln Leu Val Gln Ser Gly Ala Glu Val Lys Lys Pro Gly Glu
1               5                  10                  15

Ser Leu Arg Ile Ser Cys Lys Gly Ser Gly Tyr Thr Phe Thr Thr Tyr
                 20                 25                  30

Trp Met His Trp Val Arg Gln Ala Thr Gly Gln Gly Leu Glu Trp Met
             35                 40                  45

Gly Asn Ile Tyr Pro Gly Thr Gly Gly Ser Asn Phe Asp Glu Lys Phe
         50                 55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                        85                  90                  95

Thr Arg Trp Thr Thr Gly Thr Gly Ala Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175
```

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 9
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9
gaggtgcagc tggtgcagtc aggcgccgaa gtgaagaagc ccggcgagtc actgagaatt    60
agctgtaaag gttcaggcta caccttcact acctactgga tgcactgggt ccgccaggct   120
accggtcaag gcctcgagtg gatgggtaat atctaccccg gcaccggcgg ctctaacttc   180
gacgagaagt ttaagaatag agtgactatc accgccgata gtctactagc accgccbtat   240
atggaactgt ctagcctgag atcagaggac accgccgtct actactgcac taggtggact   300
accggcacag gcgcctactg gggtcaaggc actaccgtga ccgtgtctag cgctagcact   360
aagggcccgt ccgtgttccc cctggcacct tgtagccgga gcactagcga atccaccgct   420
gccctcggct gcctggtcaa ggattacttc ccggagcccg tgaccgtgtc ctggaacagc   480

-continued

```
ggagccctga cctccggagt gcacaccttc cccgctgtgc tgcagagctc cgggctgtac    540
tcgctgtcgt cggtggtcac ggtgccttca tctagcctgg gtaccaagac ctacacttgc    600
aacgtggacc acaagccttc aacactaag gtggacaagc gcgtcgaatc gaagtacggc     660
ccaccgtgcc cgccttgtcc cgcgccggag ttcctcggcg tccctcggt ctttctgttc     720 ccaccgaagc ccaaggacac tttgatgatt cccgcaccc ctgaagtgac atgcgtggtc     780
gtggacgtgt cacaggaaga tccggaggtg cagttcaatt ggtacgtgga tggcgtcgag    840
gtgcacaacg ccaaaaccaa gccgagggag gagcagttca actccactta ccgcgtcgtg    900
tccgtgctga cggtgctgca tcaggactgg ctgaacggga aggagtacaa gtgcaaagtg    960
tccaacaagg gacttcctag ctcaatcgaa aagaccatct cgaaagccaa gggacagccc   1020
cgggaacccc aagtgtatac cctgccaccg agccaggaag aaatgactaa gaaccaagtc   1080
tcattgactt gccttgtgaa gggcttctac ccatcggata tcgccgtgga atgggagtcc   1140
aacggccagc cggaaaacaa ctacaagacc acccctccgg tgctggactc agacggatcc   1200
ttcttcctct actcgcggct gaccgtggat aagagcagat ggcaggaggg aaatgtgttc   1260
agctgttctg tgatgcatga agccctgcac aaccactaca ctcagaagtc cctgtccctc   1320
tccctggga                                                           1329
```

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 10

Lys Ser Ser Gln Ser Leu Leu Asp Ser Gly Asn Gln Lys Asn Phe Leu
1               5                   10                  15

Thr

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 12

Gln Asn Asp Tyr Ser Tyr Pro Tyr Thr
1               5

```
<210> SEQ ID NO 13
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Gln Ser Leu Leu Asp Ser Gly Asn Gln Lys Asn Phe
1               5                   10

<210> SEQ ID NO 14
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Trp Ala Ser
1

<210> SEQ ID NO 15
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Tyr Ser Tyr Pro Tyr
1               5

<210> SEQ ID NO 16
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 17
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 17

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg taaagcccct aagctgctga tctactgggc ctctactaga   180
gaatcaggcg tgccctctag gtttagcggt agcggtagtg gcaccgactt caccttcact   240
atctctagcc tgcagcccga ggatatcgct acctactact gtcagaacga ctatagctac   300
ccctacacct tcggtcaagg cactaaggtc gagattaag                          339
```

<210> SEQ ID NO 18
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 19
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19

```
gagatcgtcc tgactcagtc acccgctacc ctgagcctga gccctggcga gcgggctaca    60
ctgagctgta atctagtca gtcactgctg gatagcggta atcagaagaa cttcctgacc    120
tggtatcagc agaagcccgg taaagcccct aagctgctga tctactgggc ctctactaga    180
gaatcaggcg tgccctctag gtttagcggt agcggtagtg gcaccgactt cacccttcact    240 atctctagcc tgcagcccga ggatatcgct acctactact gtcagaacga ctatagctac    300
ccctacacct tcggtcaagg cactaaggtc gagattaagc gtacggtggc cgctcccagc    360
gtgttcatct ccccccccag cgacgagcag ctgaagagcg gcaccgccag cgtggtgtgc    420
ctgctgaaca acttctaccc ccgggaggcc aaggtgcagt ggaaggtgga caacgccctg    480
cagagcggca acagccagga gagcgtcacc gagcaggaca gcaaggactc cacctacagc    540
ctgagcagca ccctgacccct gagcaaggcc gactacgaga agcataaggt gtacgcctgc    600
gaggtgaccc ccagggcct gtccagcccc gtgaccaaga gcttcaacag gggcgagtgc    660
```

<210> SEQ ID NO 20
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys
```

<210> SEQ ID NO 21
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg tcaagcccct agactgctga tctactgggc ctctactaga   180
gaatcaggcg tgccctctag gtttagcggt agcggtagtg gcaccgactt caccttcact   240
atctctagcc tggaagccga ggacgccgct acctactact gtcagaacga ctatagctac   300
cctacaccct tcggtcaagg cactaaggtc gagattaag                          339
```

<210> SEQ ID NO 22
<211> LENGTH: 220
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 22

```
Glu Ile Val Leu Thr Gln Ser Pro Ala Thr Leu Ser Leu Ser Pro Gly
1               5                   10                  15

Glu Arg Ala Thr Leu Ser Cys Lys Ser Ser Gln Ser Leu Leu Asp Ser
            20                  25                  30

Gly Asn Gln Lys Asn Phe Leu Thr Trp Tyr Gln Gln Lys Pro Gly Gln
        35                  40                  45

Ala Pro Arg Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Phe Thr
65                  70                  75                  80

Ile Ser Ser Leu Glu Ala Glu Asp Ala Ala Thr Tyr Tyr Cys Gln Asn
                85                  90                  95

Asp Tyr Ser Tyr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 23
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
gagatcgtcc tgactcagtc acccgctacc ctgagcctga gccctggcga gcgggctaca    60
ctgagctgta aatctagtca gtcactgctg gatagcggta atcagaagaa cttcctgacc   120
tggtatcagc agaagcccgg tcaagcccct agactgctga tctactgggc ctctactaga   180
gaatcaggcg tgccctctag gtttagcggt agcggtagtg gcaccgactt caccttcact   240
atctctagcc tggaagccga ggacgccgct acctactact gtcagaacga ctatagctac   300
ccctacacct tcggtcaagg cactaaggtc gagattaagc gtacggtggc cgctcccagc   360
gtgttcatct tcccccccag cgacgagcag ctgaagagcg gcaccgccag cgtggtgtgc   420
ctgctgaaca acttctaccc ccgggaggcc aaggtgcagt ggaaggtgga caacgccctg   480
cagagcggca acagccagga gagcgtcacc gagcaggaca gcaaggactc cacctacagc   540
ctgagcagca ccctgaccct gagcaaggcc gactacgaga agcataaggt gtacgcctgc   600
gaggtgaccc accagggcct gtccagcccc gtgaccaaga gcttcaacag gggcgagtgc   660

<210> SEQ ID NO 24
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
acctactgga tgcac                                                     15

<210> SEQ ID NO 25
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
aatatctacc ccggcaccgg cggctctaac ttcgacgaga agtttaagaa t              51

<210> SEQ ID NO 26
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
tggactaccg gcacaggcgc ctac                                           24

<210> SEQ ID NO 27
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ggctacacct tcactaccta c                                              21
```

-continued

```
<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28 tacccccggca ccggcggc                                                  18

<210> SEQ ID NO 29
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
aaatctagtc agtcactgct ggatagcggt aatcagaaga acttcctgac c              51

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
tgggcctcta ctagagaatc a                                               21

<210> SEQ ID NO 31
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
cagaacgact atagctaccc ctacacc                                         27

<210> SEQ ID NO 32
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
agtcagtcac tgctggatag cggtaatcag aagaacttc                            39

<210> SEQ ID NO 33
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 33 tgggcctct                                                                                           9

<210> SEQ ID NO 34
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
gactatagct accccctac                                                                               18

<210> SEQ ID NO 35
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val

```
                260                 265                 270
Asp Gly Val Glu Val His Asn Ala Lys Thr Lys Pro Arg Glu Glu Gln
            275                 280                 285

Phe Asn Ser Thr Tyr Arg Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

-continued

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 37

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys
    435                 440                 445

<210> SEQ ID NO 38
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
```

210                 215

<210> SEQ ID NO 39
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Gln Trp Met
        35                  40                  45

Gly Trp Ile Asn Thr Asp Ser Gly Glu Ser Thr Tyr Ala Glu Glu Phe
    50                  55                  60

Lys Gly Arg Phe Val Phe Ser Leu Asp Thr Ser Val Asn Thr Ala Tyr
65                  70                  75                  80

Leu Gln Ile Thr Ser Leu Thr Ala Glu Asp Thr Gly Met Tyr Phe Cys
                85                  90                  95

Val Arg Val Gly Tyr Asp Ala Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 40
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Ile Val Leu Thr Gln Ser Pro Ser Ser Leu Ser Ala Ser Val Gly
1               5                   10                  15

Asp Arg Val Thr Ile Thr Cys Ser Ala Arg Ser Ser Val Ser Tyr Met
            20                  25                  30

His Trp Phe Gln Gln Lys Pro Gly Lys Ala Pro Lys Leu Trp Ile Tyr
        35                  40                  45

Arg Thr Ser Asn Leu Ala Ser Gly Val Pro Ser Arg Phe Ser Gly Ser
    50                  55                  60

Gly Ser Gly Thr Ser Tyr Cys Leu Thr Ile Asn Ser Leu Gln Pro Glu
65                  70                  75                  80

Asp Phe Ala Thr Tyr Tyr Cys Gln Gln Arg Ser Ser Phe Pro Leu Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 10
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic peptide"

<400> SEQUENCE: 41

Gly Tyr Thr Phe Thr Thr Tyr Trp Met His
1               5                   10

<210> SEQ ID NO 42
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Ile Lys Leu Gly Thr Val Thr Thr Val Asp Tyr Trp Gly Gln Gly Thr
            100                 105                 110

Leu Val Thr Val Ser Ser
        115

<210> SEQ ID NO 43
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110

```
<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Ser Tyr Trp Met Tyr
1               5

<210> SEQ ID NO 45
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Arg Ile Asp Pro Asn Ser Gly Ser Thr Lys Tyr Asn Glu Lys Phe Lys
1               5                   10                  15

Asn

<210> SEQ ID NO 46
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Asp Tyr Arg Lys Gly Leu Tyr Ala Met Asp Tyr
1               5                   10

<210> SEQ ID NO 47
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Tyr Thr Phe Thr Ser Tyr
1               5

<210> SEQ ID NO 48
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asp Pro Asn Ser Gly Ser
1               5

<210> SEQ ID NO 49
<211> LENGTH: 11
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Lys Ala Ser Gln Asp Val Gly Thr Ala Val Ala
1               5                   10

<210> SEQ ID NO 50
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Trp Ala Ser Thr Arg His Thr
1               5

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Gln Tyr Asn Ser Tyr Pro Leu Thr
1               5

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Ser Gln Asp Val Gly Thr Ala
1               5

<210> SEQ ID NO 53
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Trp Ala Ser
1

<210> SEQ ID NO 54
<211> LENGTH: 6
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic peptide"

<400> SEQUENCE: 54

Tyr Asn Ser Tyr Pro Leu
1               5

<210> SEQ ID NO 55
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser
        115                 120

<210> SEQ ID NO 56
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
gaggtccagc tggtacagtc tggggctgag gtgaagaagc ctggggctac agtgaaaatc      60
tcctgcaagg tttctggcta caccttcacc agttactgga tgtactgggt gcgacaggct     120
cgtggacaac gccttgagtg gataggtagg attgatccta atagtgggag tactaagtac     180
aatgagaagt tcaagaacag attcaccatc tccagagaca attccaagaa cacgctgtat     240
cttcaaatga acagcctgag agccgaggac acggccgtgt attactgtgc aagggactat     300
agaaaggggc tctatgctat ggactactgg ggccagggca ccaccgtgac cgtgtcctcc     360

<210> SEQ ID NO 57
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57

```
gaggtccagc tggtacagtc tggggctgag gtgaagaagc ctgggggctac agtgaaaatc      60 tcctgcaagg tttctggcta caccttcacc agttactgga tgtactgggt gcgacaggct     120
cgtggacaac gccttgagtg gataggtagg attgatccta atagtgggag tactaagtac     180
aatgagaagt tcaagaacag attcaccatc tccagagaca attccaagaa cacgctgtat     240
cttcaaatga acagcctgag agccgaggac acggccgtgt attactgtgc aagggactat     300 agaaagggggc tctatgctat ggactactgg ggccagggca ccaccgtgac cgtgtcctcc    360
gcttccacca agggcccatc cgtcttcccc ctggcgccct gctccaggag cacctccgag     420
agcacagccg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacgaagacc     600
tacacctgca acgtagatca caagcccagc aacaccaagg tggacaagag agttgagtcc     660
aaatatggtc ccccatgccc accgtgccca gcacctgagt tcctgggggg accatcagtc     720
ttcctgttcc ccccaaaacc caaggacact ctcatgatct cccggacccc tgaggtcacg     780
tgcgtggtgg tggacgtgag ccaggaagac cccgaggtcc agttcaactg gtacgtggat     840
ggcgtggagg tgcataatgc caagacaaag ccgcgggagg agcagttcaa cagcacgtac     900
cgtgtggtca gcgtcctcac cgtcctgcac caggactggc tgaacggcaa ggagtacaag     960
tgcaaggtgt ccaacaaagg cctcccgtcc tccatcgaga aaaccatctc caaagccaaa    1020
gggcagcccc gagagccaca ggtgtacacc ctgcccccat cccaggagga gatgaccaag    1080
aaccaggtca gcctgacctg cctggtcaaa ggcttctacc ccagcgacat cgccgtggag    1140
tgggagagca atgggcagcc ggagaacaac tacaagacca cgcctcccgt gctggactcc    1200
gacggctcct tcttcctcta cagcaggcta accgtggaca agagcaggtg gcaggagggg    1260
aatgtcttct catgctccgt gatgcatgag gctctgcaca accactacac acagaagagc    1320
ctctccctgt ctctgggtaa a                                              1341
```

<210> SEQ ID NO 58
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys
                100                 105
```

<210> SEQ ID NO 59
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

```
gccatccagt tgacccagtc tccatcctcc ctgtctgcat ctgtaggaga cagagtcacc      60
atcacttgca aggccagtca ggatgtgggt actgctgtag cctggtacct gcagaagcca     120
gggcagtctc cacagctcct gatctattgg gcatccaccc ggcacactgg ggtcccctcg     180
aggttcagtg gcagtggatc tgggacagat ttcaccttta ccatcagtag cctggaagct     240
gaagatgctg caacatatta ctgtcagcag tataacagct atcctctcac gttcggccaa     300
gggaccaagg tggaaatcaa a                                               321
```

<210> SEQ ID NO 60
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Leu Gln Lys Pro Gly Gln Ser Pro Gln Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 61
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

```
gccatccagt tgacccagtc tccatcctcc ctgtctgcat ctgtaggaga cagagtcacc    60
atcacttgca aggccagtca ggatgtgggt actgctgtag cctggtacct gcagaagcca   120
gggcagtctc cacagctcct gatctattgg gcatccaccc ggcacactgg ggtcccctcg   180
aggttcagtg gcagtggatc tgggacagat ttcaccttta ccatcagtag cctggaagct   240
gaagatgctg caacatatta ctgtcagcag tataacagct atcctctcac gttcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 62
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met Tyr Trp Val Arg Gln Ala Arg Gly Gln Arg Leu Glu Trp Ile
        35                  40                  45

Gly Arg Ile Asp Pro Asn Ser Gly Ser Thr Lys Tyr Asn Glu Lys Phe
    50                  55                  60

Lys Asn Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Lys Gly Leu Tyr Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 63
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Tyr Thr Phe Thr Ser Tyr Trp Met Tyr
1               5                   10
```

1-(4-AMINO-5-BROMO-6-(1H-PYRAZOL-1-YL)PYRIMIDIN-2-YL)-1H-PYRAZOL-4-OL AND USE THEREOF IN THE TREATMENT OF CANCER

FIELD OF THE INVENTION

This invention relates to an active metabolite of 5-bromo-2,6-di(1H-pyrazol-1-yl)pyrimidin-4-amine, namely 1-(4-amino-5-bromo-6-(1H-pyrazol-1-yl)pyrimidin-2-yl)-1H-pyrazol-4-ol, which modulates adenosine A2a receptor. In particular, the present invention relates to pharmaceutical compositions comprising 1-(4-amino-5-bromo-6-(1H-pyrazol-1-yl)pyrimidin-2-yl)-1H-pyrazol-4-ol, as well as processes for its preparation and its use in the treatment of cancer.

BACKGROUND OF THE INVENTION

Cancer is a major public health problem in worldwide. It is currently the second leading cause of death in the United States and in several developed countries, and is expected to surpass heart diseases as the leading cause of death in the next few years. (Siegel R L, et al, Cancer Statistics, 2015, CA Cancer J Clin 2015; 65:5-29. VC 2015 American Cancer Society and references therein).

Cancer is considers a complex disease that is dictated by both cancer cell-intrinsic and cell-extrinsic processes. Several studies conducted in various in vitro and animal models including, for example, lung metastasis, human lung adenocarcinoma cells, murine melanoma cells, murine ovarian cancer cells, murine breast cancer cells, have confirmed that targeting the adenosinergic system has tremendous potential to develop different treatments. A number of lines of evidence highlight the importance of adenosine as a critical regulatory autocrine and paracrine factor that accumulates in the neoplastic microenvironment. Extracellular adenosine, which is usually present at high concentrations in cancer tissues, is a crucial mediator in the alteration of immune cell functions in cancer. This is possibly because the tightly regulated adenosine receptor pathways of immune cells undergo substantial alterations in tumours, thereby switching the functions of these cells from immune surveillance and host defence to the promotion of cancer cell transformation and growth. (Antonioli L et al, *Immunity, inflammation and cancer: a leading role for adenosine*, Nature, 842, December 2013, Volume 13, and references therein).

As it is known tumors use numerous immunosuppressive mechanisms to facilitate tumor growth (Koebel C M. et al, *Adaptive immunity maintains occult cancer in an equilibrium state*, Nature. 2007, 450, 7171:903-907 and Schreiber R D. et al, *Cancer immunoediting: Integrating immunity's roles in cancer suppression and promotion*, Science. 2011, 331, 6024:1565-1570). There are studies establishing that one such mechanism was mediated by the catabolism of extracellular AMP into immunosuppressive adenosine (Ohta A. et al, *A2A adenosine receptor protects tumors from antitumor T cells*. Proc Natl Acad Sci U S A. 2006; 103: 13132-13137 and Ohta A. et al, *A2A adenosine receptor may allow expansion of T cells lacking effector functions in extracellular adenosine-rich microenvironments*. J Immunol. 2009, 183, 9:5487-5493). Firstly, extracellular ATP will be converted to AMP by the ectoenzyme CD39. Further dephosphorylation of the AMP through the CD73 ectoenzyme will result in extracellular adenosine production.

During this process, activity of adenosine kinase is also suppressed causing the inhibition of salvage activity of this enzyme and an increase in adenosine levels. For example, under hypoxic conditions during inflammation or within tumor microenvironment, inhibition of adenosine kinase causes 15-20-fold increase in both extracellular as well as intracellular levels of adenosine (Decking U K. Et al, *Hypoxia-induced inhibition of adenosine kinase potentiates cardiac adenosine release.* Circ. Res. 1997; 81(2):154-164. doi: 10.1161/01.RES.81.2.154). The generated extracellular adenosine binds to four known cell surface receptors (A1, A2A, A2B, and A3) that are expressed on multiple immune subsets including T cells, natural killer (NK) cells, natural killer T cells, macrophages, dendritic cells, and myeloid-derived suppressor cells (MDSCs). The A2A and A2B receptor subtypes are essentially responsible for the immunosuppressive effects of adenosine. They share a common signaling pathway, both resulting in the activation of adenylate cyclase and the accumulation of intracellular cAMP. Several evidences have been further provided demonstrating that the intracellular cAMP is the signaling molecule that inhibits T-cell receptor signaling at early and late stages of T-cell receptor-triggered T-cell activating pathway. (Ohta A, Sitkovsky M, *Role of G-protein-coupled adenosine receptors in downregulation of inflammation and protection from tissue damage,* Nature, 2001, 414: 916-920).

It has been suggested that the elimination of $A_2a$ receptor genetically or the inhibition of $A_2a$ receptor signaling using $A_2a$ receptor antagonists prevents inhibition of anti-tumour T cells and improves tumour rejection (Ohta A. et al, *$A_2a$ adenosine receptor protects tumors from antitumor T cells.* Proc Natl Acad Sci U S A. 2006; 103: 13132-13137).

$A_2a$ receptor functions as a non-redundant negative regulator of activated T cells to protect normal tissues from excessive collateral inflammatory damage. It has been proposed that $A_2a$ receptor may also 'misguidedly' protect cancerous tissues. It was reasoned that if this were indeed the case, then the genetic inactivation or pharmacological antagonism of $A_2a$ receptor would prevent the inhibition of anti-tumour T cells and thereby improve tumour rejection by these de-inhibited T cells (Sitkovsky M. et al, *Adenosine $A_2a$ receptor antagonists: blockade of adenosinergic effects and T regulatory cells,* British Journal of Pharmacology, 2008, 153, S457-S464).

Lung cancer is the leading cause of cancer death around the world and it has been the most common cancer worldwide since 1985, both in terms of incidence and mortality. Globally, lung cancer is the largest contributor to new cancer diagnoses (12.4% of total new cancer cases) and to death from cancer (17.6% of total cancer deaths).

Lung cancer arises from the cells of the respiratory epithelium and can be divided into two broad categories. Small cell lung cancer (SCLC) is a highly malignant tumor derived from cells exhibiting neuroendocrine characteristics and accounts for 15% of lung cancer cases. Non-small cell lung cancer (NSCLC), which accounts for the remaining 85% of cases, is further divided into 3 major pathologic subtypes: adenocarcinoma, squamous cell carcinoma, and large cell carcinoma. Adenocarcinoma by itself accounts for 38.5% of all lung cancer cases, with squamous cell carcinoma accounting for 20% and large cell carcinoma accounting for 2.9%. In the past several decades, the incidence of adenocarcinoma has increased greatly, and adenocarcinoma has replaced squamous cell carcinoma as the most prevalent type of NSCLC. (De la Cruz, C et al, *Lung Cancer: Epidemiology, Etiology, and Prevention,* Clin Chest Med. 2011 December; 32(4)).

Particularly, in the case of NSCLC, disease stage determines the treatment, which includes surgery, radiation, platinum-based doublet chemotherapy and recently targeted therapies by interrupting signaling pathways responsible for cell proliferation and survival. Earlier stages of the disease benefit from systemic chemotherapy (platinum-doublet, taxanes, gemcitabine, pemetrexed) (Azzoli C G. et al, 2011 *Focused Update of 2009 American Society of Clinical Oncology Clinical Practice Guideline Update on Chemotherapy for Stage IV Non-Small-Cell Lung Cancer,* J Oncol Pract. 2012; 8:63-6 doi:10.1200/JOP.2011.000374), that results in modest efficacy, thus, multimodal therapeutic strategy has become an important treating option for NSCLC patients. In several studies, two or more drug combinations were proven to have superior efficacy but at the expense of added toxicity (Yoshida T. et al, *Comparison of adverse events and efficacy between gefitinib and erlotinib in patients with non-small-cell lung cancer: a retrospective analysis,* Med Oncol. 2013; 30:349).

Recently, several approaches are being developed to boost anticancer responses of T-cells and restore their ability to detect and attack cancer cells among them mAbs blocking the cytotoxic lymphocyte-associated antigen 4 (CTLA4) and the programmed cell death protein 1 (PD-1)-mediated T-cell events have been developed.

Ipilimumab, a fully human mAb against CTLA4, has shown a trend toward greater clinical benefit among patients with SQCLC (Lynch T J. et al, *Ipilimumab in combination with paclitaxel and carboplatin as first-line treatment in stage IIIB/IV non-small-cell lung cancer: Results from a randomized, double-blind, multicenter phase II study,* J Clin Oncol.2012; 30: 2046-54). The PD-1 mAbs (MEDI4735, BMS-936558, BMS-936559) have demonstrated remarkable sustained tumour regressions in the heavily pre-treated advanced NSCLC patients (Brahmer J R. et al, *Safety and activity of anti-PD-L1 antibody in patients with advanced cancer,* N Engl J Med. 2012; 366: 2455-65).

There are studies showing the alterations provoking changes in the extracellular tumor microenvironment. One of such extracellular alterations is the increased adenosine concentrations, which impair T cell mediated rejection and support angiogenesis. The study showed a significant number of lung adenocarcinomas expressing adenosine $A_2a$ receptor, supporting tests of adenosine $A_2a$ receptor antagonists as anticancer therapies. (Mediavilla-Varela, M et al, *Antagonism of adenosine $A_2a$ receptor expressed by lung adenocarcinoma tumor cells and cancer associated fibroblasts inhibits their growth,* Cancer Biology & Therapy, September 2013, 14:9, 860-868).

Despite the development of new therapeutics, NSCLC still has a 5-year survival rate in only 14% implying the need for the continuing research for novel treatments (Spira A. et al, *Multidisciplinary management of lung cancer,* N Engl J Med. 2004; 350:379-92 doi: 10.1056/NEJMra035536).

WO2011/121418, the relevant disclosure of which is incorporated herein by reference, discloses a series of aminopyrimidine derivatives as adenosine A2a receptor antagonists for the use in the treatment of neurodegenerative diseases such as Parkinson disease. Furthermore, the effectiveness of the compounds described in WO2011/121418 in the treatment of cancer was later investigated. A particular compound in this class is 5-bromo-2,6-di(1H-pyrazol-1-yl)pyrimindin-4-amine which has been found effective in the treatment of cancer. The structure of 5-bromo-2,6-di(1H-pyrazol-1-yl)pyrimindin-4-amine is shown below:

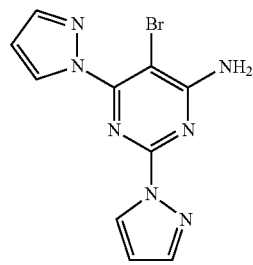 [SMILES: Nc1nc(-n2cccn2)nc(-n2cccn2)c1Br]

PCT/IB2016/054834 discloses the use of such compound alone or in combination with one or more immunotherapeutic agents in the treatment of cancer.

SUMMARY OF THE INVENTION

The instant invention relates to an active metabolite of 5-bromo-2,6-di(1H-pyrazol-1-yl)pyrimindin-4-amine, namely 1-(4-amino-5-bromo-6-(1H-pyrazol-1-yl)pyrimidin-2-yl)-1H-pyrazol-4-ol, or a pharmaceutically acceptable salt thereof. The present invention further provides the above compound in a substantially isolated form. The instant invention further provides compositions comprising 1-(4-amino-5-bromo-6-(1H-pyrazol-1-yl)pyrimidin-2-yl)-1H-pyrazol-4-ol, or a pharmaceutically acceptable salt thereof, and at least one pharmaceutically acceptable carrier.

The present invention further provides method of inhibiting adenosine A2a receptor comprising administering 1-(4-amino-5-bromo-6-(1H-pyrazol-1-yl)pyrimidin-2-yl)-1H-pyrazol-4-ol, or a pharmaceutically acceptable salt thereof. The present invention further provides a method of treating cancer in a subject in need of such treatment, comprising administering 1-(4-amino-5-bromo-6-(1H-pyrazol-1-yl)pyrimidin-2-yl)-1H-pyrazol-4-ol, or a pharmaceutically acceptable salt thereof, alone or in combination with one or more immunotherapeutic agents.

DISCLOSURE OF THE INVENTION

Figure 1:
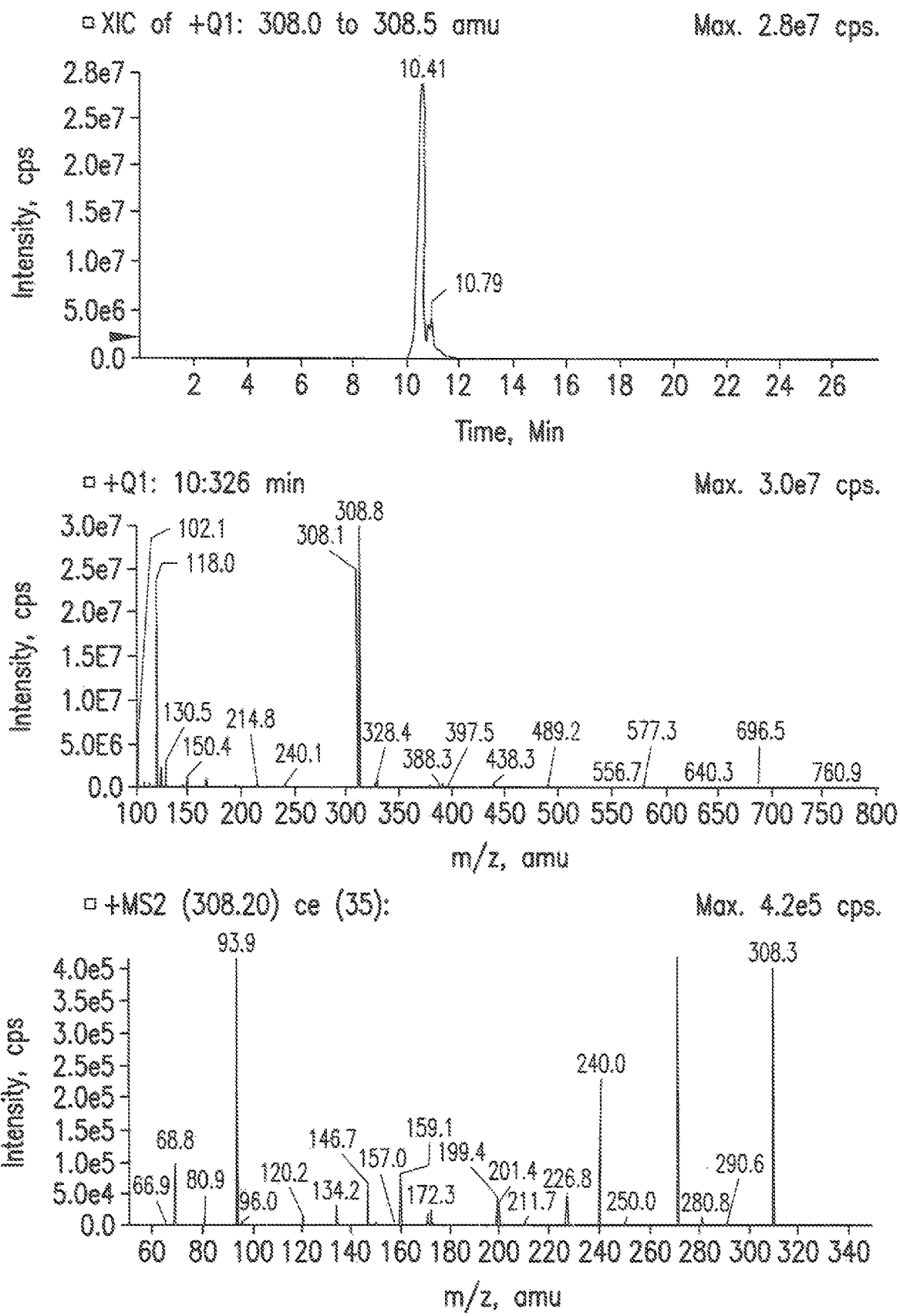
FIG. 1. illustrates XIC chromatogram, Q1 and MS/MS spectrum of 5-bromo-2,6-di(1H-pyrazol-1-yl)pyrimindin-4-amine in aqueous standard (MH+: 308).

Thus, the present invention relates in embodiment 1 to the following compound: 1-(4-amino-5-bromo-6-(1H-pyrazol-1-yl)-pyrimidin-2-yl)-1H-pyrazol-4-ol:

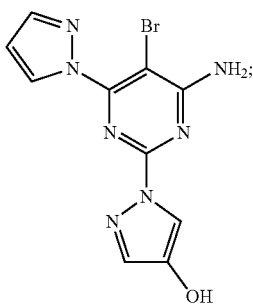 [SMILES: Nc1nc(-n2cc(O)cn2)nc(-n2cccn2)c1Br]

which is formed by the metabolism of of 5-bromo-2,6-di (1H-pyrazol-1-yl)pyrimindin-4-amine in animals, man and/or in in-vitro cellular assays.

In embodiment 2, the present invention relates to an isolated form of 1-(4-amino-5-bromo-6-(1H-pyrazol-1-yl)-pyrimidin-2-yl)-1H-pyrazol-4-ol, or a pharmaceutically acceptable salt thereof.

In a embodiment 3, the invention is a pharmaceutical composition comprising, 1-(4-amino-5-bromo-6-(1H-pyrazol-1-yl)-pyrimidin-2-yl)-1H-pyrazol-4-ol, or a pharmaceutically acceptable salt thereof, and at least one pharmaceutically acceptable excipient.

In embodiment 4, the invention is a combination, in particular a pharmaceutical combination, comprising a therapeutically effective amount of 1-(4-amino-5-bromo-6-(1H-pyrazol-1-yl)-pyrimidin-2-yl)-1H-pyrazol-4-ol, or a pharmaceutically acceptable salt thereof and one or more immunotherapeutic agents.

In embodiment 5, the invention is a method of treating cancer, in a subject in need of such treatment, the method comprising: administering to a subject in need thereof, a therapeutically effective amount of 1-(4-amino-5-bromo-6-(1H-pyrazol-1-yl)-pyrimidin-2-yl)-1H-pyrazol-4-ol , or a pharmaceutically acceptable salt thereof; alone or in combination with one or more immotherapeutic agents.

In a embodiment 6, the invention relates to the use of 1-(4-amino-5-bromo-6-(1H-pyrazol-1-yl)-pyrimidin-2-yl)-1H-pyrazol-4-ol, or a pharmaceutically acceptable salt thereof; alone or in combination with one or more immunotherapeutic agents, for the treatment of cancer.

In embodiment 7, the invention pertains to the compound 1-(4-amino-5-bromo-6-(1H-pyrazol-1-yl)-pyrimidin-2-yl)-1H-pyrazol-4-ol according to embodiment 2, or a pharmaceutically composition according to embodiment 3, for use in the treatment of cancer.

In embodiment 8, the invention pertains to a combination of 1-(4-amino-5-bromo-6-(1H-pyrazol-1-yl)-pyrimidin-2-yl)-1H-pyrazol-4-ol and one or more immunotherapeutic agents, for use in the treatment of cancer.

In embodiment 9, the invention is a method of inhibiting adenosine A2a receptor in a subject, wherein the method comprises administering to the subject a therapeutically effective amount of the 1-(4-amino-5-bromo-6-(1H-pyrazol-1-yl)-pyrimidin-2-yl)-1H-pyrazol-4-ol according to embodiment 2; or administering a pharmaceutical composition according to embodiment 3 to a subject.

In embodiment 10, the invention relates to the method of embodiment 5, a use according to embodiment 6, or the compound for use according to embodiment 7, or combination for use according to embodiment 8, wherein the cancer is selected from a lung cancer, a melanoma, a renal cancer, a liver cancer, a myeloma, a prostate cancer, a breast cancer, a colorectal cancer, a pancreatic cancer, a head and neck cancer, anal cancer, gastro-esophageal cancer, thyroid cancer, cervical cancer, a lymphoproliferative disease or a hematological cancer, T-cell lymphoma, B-cell lymphoma, a non-Hogdkin lymphoma, or a leukemia.

In embodiment 11, the invention relates to the method of embodiment 5, a use according to embodiment 6, or the compound for use according to embodiment 7, or combination for use according to embodiment 8, wherein the cancer is carcinomas, specifically lung cancer and more specifically non-small cell lung cancer.

In embodiment 12, the invention relates to the method of embodiment 5, 10 or 11, a use according to embodiment 6, 10 or 11, or the combination for use according to embodiments 9, 10 or 11, wherein one or more immunotherapeutic agents are selected from the group consisting of anti-CTLA4 antibodies, anti-PD-1 antibodies and anti-PD-L1 antibodies.

In embodiment 13, the invention relates to the method of embodiment 5, 10 or 11, a use according to embodiment 6, 10 or 11, or the combination for use according to embodiments 9, 10 or 11, wherein the immunotherapeutic agent is selected from the group consisting of: Ipilimumab, Tremelimumab, Nivolumab, Pembrolizumab, Pidilizumab (CT-011), AMP-224, AMP-514 (MEDI0680-Medimmune), MPDL3280A (Genentech Roche), MEDI4736, MSB0010718C (Merck Serono), YW243.55.S70 and MDX-1105.

In embodiment 14, the invention relates to the method of embodiment 5, 10 or 11, a use according to embodiment 6, 10 or 11, or the combination for use according to embodiments 9, 10 or 11, wherein the immunotherapeutic agents is an anti-PD-1 antibody.

In embodiment 14A, the invention relates to the method of embodiment 5, 10 or 11, a use according to embodiment 6, 10 or 11, or the combination for use according to embodiments 9, 10 or 11, wherein the immunotherapeutic agents is an anti-PD-1 antibody selected from Nivulomab, Pembrolizumab, Pidilizumab, MEDI0680 (AMP514 Medimmune), AMP224 (Medimmune), and antibodies described in US 2015/0210769)

In embodiment 15, the invention relates to the method, the use or the combination for use according to embodiment 14, wherein the anti-PD-1 antibody comprises:

(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;

(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;

(c) a VH comprising a VHCDR1 amino acid sequence of SEQ ID NO: 41, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or (d) a VH comprising a VHCDR1 amino acid sequence of SEQ ID NO: 41; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

In embodiment 16, the invention pertains to the method, the use or the combination for use according to embodiment 14, wherein the anti-PD-1 comprises a VH comprising the amino acid sequence of SEQ ID NO: 6 and a VL comprising the amino acid sequence of SEQ ID NO: 20.

In embodiment 17, the invention pertains to the method, the use or the combination for use according to embodiment 14, wherein the anti-PD-1 antibody comprises a heavy chain comprising the amino acid sequence of SEQ ID NO: 8 and a light chain comprising the amino acid sequence of SEQ ID NO: 22.

In embodiment 18, the invention pertains to the method, the use or the combination for use according to embodiment 14, wherein the anti-PD-1 antibody comprises a VH comprising the amino acid sequence of SEQ ID NO: 6 and a VL comprising the amino acid sequence of SEQ ID NO: 16.

In embodiment 19, the invention pertains to the method, the use or the combination for use according to embodiment 14, wherein the anti-PD-1 antibody comprises a heavy chain comprising the amino acid sequence of SEQ ID NO: 8 and a light chain comprising the amino acid sequence of SEQ ID NO: 18.

In embodiment 20, the invention pertains to the method, the use or the combination for use according to any one of embodiments 14-19, wherein the anti-PD-1 antibody molecule is administered at a dose of about 300 mg once every three weeks.

In embodiment 21, the invention pertains to the method, the use or the combination for use according to any one of embodiments 14-19, wherein the anti-PD-1 antibody molecule is administered at a dose of about 400 mg once every four weeks.

In embodiment 22, the invention relates to the method of embodiment 5, 10 or 11, a use according to embodiment 6, 10 or 11, or the combination for use according to embodiments 9, 10 or 11, wherein the immunotherapeutic agents is is an anti-PD-L1 antibody.

In embodiment 22A, the invention relates to the method, the use or the combination for use according to embodiment 22, wherein the anti PD-L1 antibody molecule is selected from YW243.55.S70, MPDL3280A, MEDI-4736, MSB-0010718C, MDX-1105 and an anti PD-L1 antibody described in US 2016/0108123.

In embodiment 23, the invention relates to the method, the use or the combination for use according to embodiment 22, wherein the anti PD-L1 antibody molecule comprises:

(a) a heavy chain variable region (VH) comprising a VHCDR1 amino acid sequence of SEQ ID NO: 47, a VHCDR2 amino acid sequence of SEQ ID NO: 48, and a VHCDR3 amino acid sequence of SEQ ID NO: 46; and a light chain variable region (VL) comprising a VLCDR1 amino acid sequence of SEQ ID NO: 52, a VLCDR2 amino acid sequence of SEQ ID NO: 53, and a VLCDR3 amino acid sequence of SEQ ID NO: 54;

(b) a VH comprising a VHCDR1 amino acid sequence of SEQ ID NO: 44; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51;

(c) a VH comprising a VHCDR1 amino acid sequence of SEQ ID NO: 63, a VHCDR2 amino acid sequence of SEQ ID NO: 48, and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54; or (d) a VH comprising a VHCDR1 amino acid sequence of SEQ ID NO: 63; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51.

In embodiment 24, the invention relates to the method, the use or the combination for use according to embodiment 22, wherein the anti PD-L1 antibody molecule comprises a heavy chain variable domain comprising the amino acid sequence of SEQ ID NO: 55 and a light chain variable domain comprising the amino acid sequence of SEQ ID NO: 58.

In embodiment 25, the invention relates to the method, the use or the combination for use according to any one of embodiments 12-24, wherein immunotherapeutic agent is administered together in a single composition or administered separately in two or more different compositions forms.

In embodiment 26, the invention pertains to the method the method, the use or the combination for use according to any one of embodiments 12-24 wherein the immunotherapeutic agent is administered concurrently with, prior to, or subsequent to, the compound: -(4-amino-5-bromo-6-(1H-pyrazol-1-yl)-pyrimidin-2-yl)-1H-pyrazol-4-ol.

In embodiment 27, the invention is a process of making 1-(4-amino-5-bromo-6-(1H-pyrazol-1-yl)-pyrimidin-2-yl)-1H-pyrazol-4-ol according to Example 1.

Definition:

As used in the present document the term cancer is used to designate a group of diseases involving abnormal cell growth with the potential to invade or spread to other parts of the body. Cancers are classified by the type of cell that the tumor cells resemble and is therefore presumed to be the origin of the tumor. These types include carcinoma, sarcoma, lymphoma and leukemia, germ cell tumor and blastoma.

As used in the present document the term carcinoma is used to designate cancers derived from epithelial cells. This group includes many of the most common cancers, particularly in the aged, and include nearly all those developing in the breast, prostate, lung, pancreas, and colon.

For example the term "cancer" includes but is not limited to, a solid tumor, a hematological cancer (e.g., leukemia, lymphoma, myeloma, e.g., multiple myeloma), and a metastatic lesion. In one embodiment, the cancer is a solid tumor. Examples of solid tumors include malignancies, e.g., sarcomas and carcinomas, e.g., adenocarcinomas of the various organ systems, such as those affecting the lung, breast, ovarian, lymphoid, gastrointestinal (e.g., colon), anal, genitals and genitourinary tract (e.g., renal, urothelial, bladder cells, prostate), pharynx, CNS (e.g., brain, neural or glial cells), head and neck, skin (e.g., melanoma), and pancreas, as well as adenocarcinomas which include malignancies such as colon cancers, rectal cancer, renal-cell carcinoma, liver cancer, non-small cell lung cancer, cancer of the small intestine and cancer of the esophagus. The cancer may be at an early, intermediate, late stage or metastatic cancer.

In one embodiment, the cancer is chosen from a lung cancer (e.g., a non-small cell lung cancer (NSCLC) (e.g., a NSCLC with squamous and/or non-squamous histology, or a NSCLC adenocarcinoma)), a melanoma (e.g., an advanced melanoma), a renal cancer (e.g., a renal cell carcinoma), a liver cancer, a myeloma (e.g., a multiple myeloma), a prostate cancer, a breast cancer (e.g., a breast cancer that does not express one, two or all of estrogen receptor, progesterone receptor, or Her2/neu, e.g., a triple negative breast cancer), a colorectal cancer, a pancreatic cancer, a head and neck cancer (e.g., head and neck squamous cell carcinoma (HNSCC), anal cancer, gastro-esophageal cancer, thyroid cancer, cervical cancer, a lymphoproliferative disease (e.g., a post-transplant lymphoproliferative disease) or a hematological cancer, T-cell lymphoma, B-cell lymphoma, a non-Hogdkin lymphoma, or a leukemia (e.g., a myeloid leukemia or a lymphoid leukemia).

In another embodiment, the cancer can be, e.g., a cancer described herein, such as lung cancer (squamous), lung cancer (adenocarcinoma), head and neck cancer, cervical cancer (squamous), stomach cancer, thyroid cancer, melanoma, nasopharyngeal cancer (e.g., differentiated or undifferentiated metastatic or locally recurrent nasopharyngeal carcinoma), or breast cancer.

In another embodiment, the cancer is chosen form a carcinoma (e.g., advanced or metastatic carcinoma), melanoma or a lung carcinoma, e.g., a non-small cell lung carcinoma.

In one embodiment, the cancer is a lung cancer, e.g., a non-small cell lung cancer or small cell lung cancer.

As used in the present document the term lung cancer (also known as carcinoma of the lung or pulmonary carcinoma) is used to designate malignant lung tumors characterized by uncontrolled cell growth in tissues of the lung.

As used in the present document the term non-small-cell lung carcinoma (NSCLC) is used to designate any type of lung cancer other than small cell lung carcinoma (SCLC).

As used in the present document the term immunotherapeutic treatment refers to a broad class of therapies designated to elicit immune-mediated destruction of tumor cells. In said therapies are used immunotherapeutic agents.

As used in the present document the term immunotherapeutic agents refer to compounds useful to carrying out immunotherapeutic treatment of cancer, such as agent selected from the group consisting of anti-CTLA4 antibodies, such as Ipilimumab and Tremelimumab, anti-PD-1 antibodies such as MDX-1106, MK3475, CT-011, AMP-224 or an anti-PD-1 antibody molecule as described in WO2015/112900; and anti-PD-L1 antibodies such as MEDI4736, MDX-1105 or an anti-PD-L1 antibody described in US 2016/0108123.

As used herein, the term "Programmed Death 1" or "PD-1" include isoforms, mammalian, e.g., human PD-1, species homologs of human PD-1, and analogs comprising at least one common epitope with PD-1. The amino acid sequence of PD-1, e.g., human PD-1, is known in the art, e.g., Shinohara T et al. (1994) *Genomics* 23(3):704-6; Finger LR, et al. *Gene* (1997) 197(1-2):177-87.

As used herein, the term "Programmed Death Ligand 1" or "PD-L1" include isoforms, mammalian, e.g., human PD-L1, species homologs of human PD-1, and analogs comprising at least one common epitope with PD-L1. The amino acid sequence of PD-L1, e.g., human PD-1, is known in the art, e.g., Dong et al. (1999) *Nat Med.* 5(12):1365-9; Freeman et al. (2000) *J Exp Med.* 192(7):1027-34).

By "isolated form" we mean that the compound is free from any of the components that would normally accompany it when it is formed metabolically in vivo. For example, it is free of any biological matter, such as serum components, as well as other metabolites of 5-bromo-2,6-di(1H-pyrazol-1-yl)pyrimindin-4-amine formed in vivo. Suitably, the compound is in a purified and isolated form. By "purified" we mean that the compound is conveniently greater that 75% pure, more conveniently greater than 90% pure, and preferably greater than 95% pure and most preferably greater than 98% pure.

As used herein the term "combination" refers to either a fixed combination in one dosage unit form, or a combined administration where a compound of Formula I and a combination partner (i.e. an immunotherapeutic agent) may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration.

The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time.

The term "pharmaceutical combination" and "combination product" are used interchangeably and refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect. The term "fixed combination" means that the compound of Formula I and a combination partner (i.e. immunotherapeutic agent), are both administered to a patient simultaneously in the form of a single entity or dosage.

The term "non-fixed combination" means that the compound of Formula I and a combination partner (i.e. the immunotherapeutic agent), are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent. In a preferred embodiment, the pharmaceutical combination is a non-fixed combination.

The term "combination therapy" refers to the administration of two or more therapeutic agents to treat a cancer as described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, and basic ion exchange resins, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention includes all pharmaceutically acceptable isotopically-labeled compounds of the invention, i.e. compounds of the first through seventieth embodiments, wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labeled compounds of the first through seventieth embodiments, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. In certain compounds of the first through seventieth embodiments, residues $R_9$ or the ring formed by the combination of $R_8$ and $R_9$ may comprise one or more deuterium atoms to improve metabolic stability of the compound in vivo.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the first through seventieth embodiments can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by adenosine A2a receptor thereof, or (ii) associated with adenosine or the activity of adenosine A2a receptor, or (iii) characterized by abnormal activity of adenosine A2a receptor; or (2) reducing or inhibiting the activity of adenosine A2a receptor thereof. In another non-limiting embodiment, the term "a therapeutically effective amount" refers to the amount of the compound of Formula I that, when administered to a cell, or a tissue, or a non-cellular biological material, or a medium, is effective to at least partially reducing or inhibiting the activity of $A_2a$ receptor; or at least partially reducing or inhibiting the expression of $A_2a$ receptor.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compound of the present invention is either obtained in the free form, as a salt thereof, or as prodrug derivatives thereof.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry,* Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety).

Exemplary prodrugs are, e.g., O-acyl derivatives of alcohols or arylalcohol. Preferred are pharmaceutically acceptable ester derivatives convertible by solvolysis under physiological conditions. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs,* Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

Pharmaceutical Composition, Combination, Dosage and Administration

In another aspect, the present invention provides a pharmaceutical composition comprising a compound of the present invention and a carrier, e.g., a pharmaceutically acceptable carrier. The pharmaceutical composition can be formulated for particular routes of administration such as oral administration, ophthalmic administration (e.g., topical administration, intravitreal injection, implant (including intravitreal, transscleral, sub-Tenon, and the like, depot or the like), and parenteral administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
  a) diluents, e.g., lactose, dextrose, sucrose, mannitol, sorbitol, cellulose and/or glycine;
  b) lubricants, e.g., silica, talcum, stearic acid, its magnesium or calcium salt and/or polyethyleneglycol; for tablets also
  c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Certain injectable compositions include ocular implants and ocular depot formulations which are suitable for intraocular, periocular, subconjunctival and/or sub-tenon administration. Typicaly injectable compositions comprise a compound of the first through seventieth embodiments, in combination with a biocompatible or biodegradable polymeric material.

The present invention further provides anhydrous pharmaceutical compositions and dosage forms comprising the compounds of the present invention as active ingredients, since water may facilitate the degradation of certain compounds. Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

In a preferred embodiment, 1-(4-amino-5-bromo-6-(1H-pyrazol-1-yl)pyrimidin-2-yl)-1H-pyrazol-4-ol, or pharmaceutically acceptable salt, for use in the treatment of cancer are for administration by parenteral or oral route, preferably by oral route.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In other embodiments, a pharmaceutical composition is provided which comprises at least one compound according to the first through seventieth embodiments and at least one carrier.

Therapeutic Kits

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of Formula I and the other immunotherapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of 1-(4-amino-5-bromo-6-(1H-pyrazol-1-yl)pyrimidin-2-yl)-1H-pyrazol-4-ol, or a pharmaceutically acceptable salt thereof, for treating cancer, wherein the medicament is prepared for administration with another immunotherapeutic agent. The invention also provides the use of an immunotherapeutic agent for treating cancer, wherein the medicament is administered with 1-(4-amino-5-bromo-6-(1H-pyrazol-1-yl)pyrimidin-2-yl)-1H-pyrazol-4-ol, or a pharmaceutically acceptable salt thereof.

The invention also provides 1-(4-amino-5-bromo-6-(1H-pyrazol-1-yl)pyrimidin-2-yl)-1H-pyrazol-4-ol, or a pharmaceutically acceptable salt thereof, for use in a method of treating cancer, wherein 1-(4-amino-5-bromo-6-(1H-pyrazol-1-yl)pyrimidin-2-yl)-1H-pyrazol-4-ol is prepared for administration with another immunotherapeutic agent. The invention also provides another immunotherapeutic agent for use in a method of treating cancer, wherein the other immunotherapeutic agent is prepared for administration with 1-(4-amino-5-bromo-6-(1H-pyrazol-1-yl)pyrimidin-2-yl)-1H-pyrazol-4-ol. The invention also provides 1-(4-amino-5-bromo-6-(1H-pyrazol-1-yl)pyrimidin-2-yl)-1H-pyrazol-4-ol for use in a method of treating cancer, wherein 1-(4-amino-5-bromo-6-(1H-pyrazol-1-yl)pyrimidin-2-yl)-1H-pyrazol-4-ol is administered with another immunotherapeutic agent. The invention also provides another immunotherapeutic agent for use in a method of treating cancer, wherein the other therapeutic agent is administered with 1-(4-amino-5-bromo-6-(1H-pyrazol-1-yl)pyrimidin-2-yl)-1H-pyrazol-4-ol.

The invention also provides the use of 1-(4-amino-5-bromo-6-(1H-pyrazol-1-yl)pyrimidin-2-yl)-1H-pyrazol-4-ol, for treating cancer, wherein the patient has previously (e.g. within 24 hours) been treated with another immunotherapeutic agent. The invention also provides the use of another immunotherapeutic agent for treating cancer, wherein the patient has previously (e.g. within 24 hours) been treated with a 1-(4-amino-5-bromo-6-(1H-pyrazol-1-yl)pyrimidin-2-yl)-1H-pyrazol-4-ol; or a pharmaceutically acceptable salt thereof.

Combination Therapy

In one embodiment, a pharmaceutical combination (or combination product) comprises a compound of formula (I) or a pharmaceutically acceptable salt or co-crystal thereof, and one or more immunotherapeutic agents selected from the group consisting of anti-CTLA4 antibodies, such as Ipilimumab and Tremelimumab, anti-PD-1 antibodies such as MDX-1106 (Nivolumab), MK3475 (Pembrolizumab), CT-011 (Pidilizumab), AMP-224, AMP-514 (MEDI0680 Medimmune)or an anti-PD-1 antibody molecule as described in WO2015/112900 (US2015/0210769); and anti-PD-L1 antibodies such as MPDL3280A, MEDI4736, MSB0010718C (Merch Sorono), YW243.55.S70, MDX-1105 or an anti-PD-L1 antibody molecules are disclosed in US 2016/0108123, filed Oct. 13, 2015, entitled "Antibody Molecules to PD-L1 and Uses Thereof".

The components of the combination product are in the same formulation or in separate formulations.

In a preferred embodiment the combination product comprises a compound of formula (I) or a pharmaceutically acceptable salt or co-crystal thereof, and one or more immunotherapeutic agent useful in the treatment of cancer, specifically in immunotherapeutic treatment of cancer, such agent is selected from the group consisting of anti-PD-1PD-1 antibodies such as MDX-1106, MK3475, CT-011, AMP-224 or an anti-PD-1 antibody molecule as described in WO2015/112900 (US2015/0210769); and anti-PD-L1 antibodies such as MPDL3280A, MEDI4736, MDX-1105 or an anti-PD-L1 antibody molecules are disclosed in US 2016/0108123.

Examples of Anti PD-1 Antibody Molecule

In a preferred embodiment, the combination product comprises a compound of Formula (I) or a pharmaceutically acceptable salt or co-crystal thereof, and an anti-PD-1 antibody molecule such as those described herein.

PD-1 is a CD28/CTLA-4 family member expressed, e.g., on activated $CD4^+$ and $CD8^+$ T cells, $T_{regs}$, and B cells. It negatively regulates effector T cell signaling and function. PD-1 is induced on tumor-infiltrating T cells, and can result in functional exhaustion or dysfunction (Keir et al. (2008) *Annu. Rev. Immunol.* 26:677-704; Pardoll et al. (2012) *Nat Rev Cancer* 12(4):252-64). PD-1 delivers a coinhibitory signal upon binding to either of its two ligands, Programmed Death-Ligand 1 (PD-L1) or Programed Death-Ligand 2 (PD-L2). PD-L1 is expressed on a number of cell types, including T cells, Natural killer (NK) cells, macrophages, dendritic cells (DCs), B cells, epithelial cells, vascular endothelial cells, as well as many types of tumors. High expression of PD-L1 on murine and human tumors has been linked to poor clinical outcomes in a variety of cancers (Keir et al. (2008) *Annu. Rev. Immunol.* 26:677-704; Pardoll et al. (2012) *Nat Rev Cancer* 12(4):252-64). PD-L2 is expressed on dendritic cells, macrophages, and some tumors. Blockade of the PD-1 pathway has been pre-clinically and clinically validate for cancer immunotherapy. Both preclinical and clinical studies have demonstrated that anti-PD-1 blockade can restore activity of effector T cells and results in robust anti-tumor response. For example, blockade of PD-1 pathway can restore exhausted/dysfunctional effector T cell function (e.g. proliferation, IFN-g secretion, or cytolytic function) and/or inhibit $T_{reg}$ cell function (Keir et al. (2008) *Annu. Rev. Immunol.* 26:677-704; Pardoll et al. (2012) *Nat Rev Cancer* 12(4):252-64). Blockade of the PD-1 pathway can be effected with an antibody, an antigen binding fragment thereof, an immunoadhesin, a fusion protein, or oligopeptide of PD-1, PD-L1 and/or PD-L2.

In one embodiment, the PD-1 inhibitor is an anti-PD-1 antibody molecule. In one embodiment, the PD-1 inhibitor is an anti-PD-1 antibody molecule as described in US 2015/0210769, published on Jul. 30, 2015, entitled "Antibody Molecules to PD-1 and Uses Thereof," incorporated by reference in its entirety.

In one embodiment, the anti-PD-1 antibody molecule comprises at least one, two, three, four, five or six complementarity determining regions (CDRs) (or collectively all of the CDRs) from a heavy and light chain variable region comprising an amino acid sequence shown in Table A (e.g., from the heavy and light chain variable region sequences of BAP049-Clone-E or BAP049-Clone-B disclosed in Table A), or encoded by a nucleotide sequence shown in Table A. In some embodiments, the CDRs are according to the Kabat definition (e.g., as set out in Table A). In some embodiments, the CDRs are according to the Chothia definition (e.g., as set out in Table A). In some embodiments, the CDRs are according to the combined CDR definitions of both Kabat and Chothia (e.g., as set out in Table A). In one embodiment, the combination of Kabat and Chothia CDR of VH CDR1 comprises the amino acid sequence GYTFTTYWMH (SEQ ID NO: 41). In one embodiment, one or more of the CDRs (or collectively all of the CDRs) have one, two, three, four, five, six or more changes, e.g., amino acid substitutions (e.g., conservative amino acid substitutions) or deletions, relative to an amino acid sequence shown in Table A, or encoded by a nucleotide sequence shown in Table A.

In one embodiment, the anti-PD-1 antibody molecule comprises a heavy chain variable region (VH) comprising a VHCDR1 amino acid sequence of SEQ ID NO: 1, a VHCDR2 amino acid sequence of SEQ ID NO: 2, and a VHCDR3 amino acid sequence of SEQ ID NO: 3; and a light chain variable region (VL) comprising a VLCDR1 amino acid sequence of SEQ ID NO: 10, a VLCDR2 amino acid sequence of SEQ ID NO: 11, and a VLCDR3 amino acid sequence of SEQ ID NO: 12, each disclosed in Table A.

In one embodiment, the antibody molecule comprises a VH comprising a VHCDR1 encoded by the nucleotide sequence of SEQ ID NO: 24, a VHCDR2 encoded by the nucleotide sequence of SEQ ID NO: 25, and a VHCDR3 encoded by the nucleotide sequence of SEQ ID NO: 26; and a VL comprising a VLCDR1 encoded by the nucleotide sequence of SEQ ID NO: 29, a VLCDR2 encoded by the nucleotide sequence of SEQ ID NO: 30, and a VLCDR3 encoded by the nucleotide sequence of SEQ ID NO: 31, each disclosed in Table A.

In one embodiment, the anti-PD-1 antibody molecule comprises a VH comprising the amino acid sequence of SEQ ID NO: 6, or an amino acid sequence at least 85%, 90%, 95%, or 99% identical or higher to SEQ ID NO: 6. In one embodiment, the anti-PD-1 antibody molecule comprises a VL comprising the amino acid sequence of SEQ ID NO: 20, or an amino acid sequence at least 85%, 90%, 95%, or 99% identical or higher to SEQ ID NO: 20. In one embodiment, the anti-PD-1 antibody molecule comprises a VL comprising the amino acid sequence of SEQ ID NO: 16, or an amino acid sequence at least 85%, 90%, 95%, or 99% identical or higher to SEQ ID NO: 16. In one embodiment, the anti-PD-1 antibody molecule comprises a VH comprising the amino acid sequence of SEQ ID NO: 6 and a VL comprising the amino acid sequence of SEQ ID NO: 20. In one embodiment, the anti-PD-1 antibody molecule comprises a VH comprising the amino acid sequence of SEQ ID NO: 6 and a VL comprising the amino acid sequence of SEQ ID NO: 16.

In one embodiment, the antibody molecule comprises a VH encoded by the nucleotide sequence of SEQ ID NO: 7, or a nucleotide sequence at least 85%, 90%, 95%, or 99% identical or higher to SEQ ID NO: 7. In one embodiment, the antibody molecule comprises a VL encoded by the nucleotide sequence of SEQ ID NO: 21 or 17, or a nucleotide sequence at least 85%, 90%, 95%, or 99% identical or higher to SEQ ID NO: 21 or 17. In one embodiment, the antibody molecule comprises a VH encoded by the nucleotide sequence of SEQ ID NO: 7 and a VL encoded by the nucleotide sequence of SEQ ID NO: 21 or 17.

In one embodiment, the anti-PD-1 antibody molecule comprises a heavy chain comprising the amino acid sequence of SEQ ID NO: 8, or an amino acid sequence at least 85%, 90%, 95%, or 99% identical or higher to SEQ ID NO: 8. In one embodiment, the anti-PD-1 antibody molecule comprises a light chain comprising the amino acid sequence of SEQ ID NO: 22, or an amino acid sequence at least 85%, 90%, 95%, or 99% identical or higher to SEQ ID NO: 22. In one embodiment, the anti-PD-1 antibody molecule comprises a light chain comprising the amino acid sequence of SEQ ID NO: 18, or an amino acid sequence at least 85%, 90%, 95%, or 99% identical or higher to SEQ ID NO: 18.

In one embodiment, the anti-PD-1 antibody molecule comprises a heavy chain comprising the amino acid sequence of SEQ ID NO: 8 and a light chain comprising the amino acid sequence of SEQ ID NO: 22. In one embodiment, the anti-PD-1 antibody molecule comprises a heavy chain comprising the amino acid sequence of SEQ ID NO: 8 and a light chain comprising the amino acid sequence of SEQ ID NO: 18.

In one embodiment, the antibody molecule comprises a heavy chain encoded by the nucleotide sequence of SEQ ID NO: 9, or a nucleotide sequence at least 85%, 90%, 95%, or 99% identical or higher to SEQ ID NO: 9. In one embodiment, the antibody molecule comprises a light chain encoded by the nucleotide sequence of SEQ ID NO: 23 or 19, or a nucleotide sequence at least 85%, 90%, 95%, or 99% identical or higher to SEQ ID NO: 23 or 19. In one embodiment, the antibody molecule comprises a heavy chain encoded by the nucleotide sequence of SEQ ID NO: 9 and a light chain encoded by the nucleotide sequence of SEQ ID NO: 23 or 19.

The antibody molecules described herein can be made by vectors, host cells, and methods described in US 2015/0210769, incorporated by reference in its entirety.

Definitions

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains.* In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL.

Generally, unless specifically indicated, the anti-PD-1 antibody molecules can include any combination of one or more Kabat CDRs and/or Chothia CDRs, e.g., described in Table A. In one embodiment, the following definitions are used for the anti-PD-1 antibody molecules described in Table A: HCDR1 according to the combined CDR definitions of both Kabat and Chothia, and HCCDRs 2-3 and LCCDRs 1-3 according the CDR definition of Kabat. Under all definitions, each VH and VL typically includes three CDRs and four FRs, arranged from amino-terminus to carboxy-terminus in the following order: FR1, CDR1, FR2, CDR2, FR3, CDR3, FR4.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See www.ncbi.nlm.nih.gov.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

TABLE A

Amino acid and nucleotide sequences of exemplary anti-PD-1 antibody molecules

| BAP049-Clone-B HC | | | |
|---|---|---|---|
| SEQ ID NO: 1 | (Kabat) | HCDR1 | TYWMH |
| SEQ ID NO: 2 | (Kabat) | HCDR2 | NIYPGTGGSNFDEKFKN |
| SEQ ID NO: 3 | (Kabat) | HCDR3 | WTTGTGAY |
| SEQ ID NO: 4 | (Chothia) | HCDR1 | GYTFTTY |
| SEQ ID NO: 5 | (Chothia) | HCDR2 | YPGTGG |
| SEQ ID NO: 3 | (Chothia) | HCDR3 | WTTGTGAY |

TABLE A-continued

Amino acid and nucleotide sequences of exemplary anti-PD-1 antibody molecules

| SEQ ID NO: 6 | VH | EVQLVQSGAEVKKPGESLRISCKGSGY<br>TFTTYWMHWVRQATGQGLEWMGNIYP<br>GTGGSNFDEKFKNRVTITADKSTSTAY<br>MELSSLRSEDTAVYYCTRWTTGTGAY<br>WGQGTTVTVSS |
|---|---|---|
| SEQ ID NO: 7 | DNA VH | GAGGTGCAGCTGGTGCAGTCAGGCG<br>CCGAAGTGAAGAAGCCCGGCGAGTC<br>ACTGAGAATTAGCTGTAAAGGTTCAG<br>GCTACACCTTCACTACCTACTGGATG<br>CACTGGGTCCGCCAGGCTACCGGTCA<br>AGGCCTCGAGTGGATGGGTAATATCT<br>ACCCCGGCACCGGCGGCTCTAACTTC<br>GACGAGAAGTTTAAGAATAGAGTGAC<br>TATCACCGCCGATAAGTCTACTAGCA<br>CCGCCTATATGGAACTGTCTAGCCTG<br>AGATCAGAGGACACCGCCGTCTACTA<br>CTGCACTAGGTGGACTACCGGCACAG<br>GCGCCTACTGGGGTCAAGGCACTACC<br>GTGACCGTGTCTAGC |
| SEQ ID NO: 8 | HC | EVQLVQSGAEVKKPGESLRISCKGSGY<br>TFTTYWMHWVRQATGQGLEWMGNIYP<br>GTGGSNFDEKFKNRVTITADKSTSTAY<br>MELSSLRSEDTAVYYCTRWTTGTGAY<br>WGQGTTVTVSSASTKGPSVFPLAPCSR<br>STSESTAALGCLVKDYFPEPVTVSWNS<br>GALTSGVHTFPAVLQSSGLYSLSSVVTV<br>PSSSLGTKTYTCNVDHKPSNTKVDKRV<br>ESKYGPPCPPCPAPEFLGGPSVFLFPP<br>KPKDTLMISRTPEVTCVVVDVSQEDPE<br>VQFNWYVDGVEVHNAKTKPREEQFNS<br>TYRVVSVLTVLHQDWLNGKEYKCKVSN<br>KGLPSSIEKTISKAKGQPREPQVYTLPP<br>SQEEMTKNQVSLTCLVKGFYPSDIAVE<br>WESNGQPENNYKTTPPVLDSDGSFFLY<br>SRLTVDKSRWQEGNVFSCSVMHEALH<br>NHYTQKSLSLSLG |
| SEQ ID NO: 9 | DNA HC | GAGGTGCAGCTGGTGCAGTCAGGCG<br>CCGAAGTGAAGAAGCCCGGCGAGTC<br>ACTGAGAATTAGCTGTAAAGGTTCAG<br>GCTACACCTTCACTACCTACTGGATG<br>CACTGGGTCCGCCAGGCTACCGGTCA<br>AGGCCTCGAGTGGATGGGTAATATCT<br>ACCCCGGCACCGGCGGCTCTAACTTC<br>GACGAGAAGTTTAAGAATAGAGTGAC<br>TATCACCGCCGATAAGTCTACTAGCA<br>CCGCCTATATGGAACTGTCTAGCCTG<br>AGATCAGAGGACACCGCCGTCTACTA<br>CTGCACTAGGTGGACTACCGGCACAG<br>GCGCCTACTGGGGTCAAGGCACTACC<br>GTGACCGTGTCTAGCGCTAGCACTAA<br>GGGCCCGTCCGTGTTCCCCCTGGCA<br>CCTTGTAGCCGGAGCACTAGCGAATC<br>CACCGCTGCCCTCGGCTGCCTGGTCA<br>AGGATTACTTCCCGGAGCCCGTGACC<br>GTGTCCTGGAACAGCGGAGCCCTGAC<br>CTCCGGAGTGCACACCTTCCCCGCTG<br>TGCTGCAGAGCTCCGGGCTGTACTCG<br>CTGTCGTCGGTGGTCACGGTGCCTTC<br>ATCTAGCCTGGGTACCAAGACCTACA<br>CTTGCAACGTGGACCACAAGCCTTCC<br>AACACTAAGGTGGACAAGCGCGTCGA<br>ATCGAAGTACGGCCCACCGTGCCCGC<br>CTTGTCCCGCGCCGGAGTTCCTCGGC<br>GGTCCCTCGGTCTTTCTGTTCCCACC<br>GAAGCCCAAGGACACTTTGATGATTT<br>CCCGCACCCCTGAAGTGACATGCGTG<br>GTCGTGGACGTGTCACAGGAAGATCC<br>GGAGGTGCAGTTCAATTGGTACGTGG<br>ATGGCGTCGAGGTGCACAACGCCAAA<br>ACCAAGCCGAGGGAGGAGCAGTTCAA<br>CTCCACTTACCGCGTCGTGTCCGTGC<br>TGACGGTGCTGCATCAGGACTGGCTG<br>AACGGGAAGGAGTACAAGTGCAAAGT<br>GTCCAACAAGGGACTTCCTAGCTCAA |

TABLE A-continued

Amino acid and nucleotide sequences of exemplary anti-PD-1 antibody molecules

| | | |
|---|---|---|
| | | TCGAAAAGACCATCTCGAAAGCCAAG GGACAGCCCCGGGAACCCCAAGTGT ATACCCTGCCACCGAGCCAGGAAGAA ATGACTAAGAACCAAGTCTCATTGACT TGCCTTGTGAAGGGCTTCTACCCATC GGATATCGCCGTGGAATGGGAGTCCA ACGGCCAGCCGGAAAACAACTACAAG ACCACCCCTCCGGTGCTGGACTCAGA CGGATCCTTCTTCCTCTACTCGCGGC TGACCGTGGATAAGAGCAGATGGCAG GAGGGAAATGTGTTCAGCTGTTCTGT GATGCATGAAGCCCTGCACAACCACT ACACTCAGAAGTCCCTGTCCCTCTCC CTGGGA |

BAP049-Clone-B LC

| SEQ ID NO: 10 (Kabat) | LCDR1 | KSSQSLLDSGNQKNFLT |
|---|---|---|
| SEQ ID NO: 11 (Kabat) | LCDR2 | WASTRES |
| SEQ ID NO: 12 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPY |
| SEQ ID NO: 16 | VL | EIVLTQSPATLSLSPGERATLSCKSSQS LLDSGNQKNFLTWYQQKPGKAPKLLIY WASTRESGVPSRFSGSGSGTDFTFTIS SLQPEDIATYYCQNDYSYPYTFGQGTK VEIK |
| SEQ ID NO: 17 | DNA VL | GAGATCGTCCTGACTCAGTCACCCGC TACCCTGAGCCTGAGCCCTGGCGAGC GGGCTACACTGAGCTGTAAATCTAGT CAGTCACTGCTGGATAGCGGTAATCA GAAGAACTTCCTGACCTGGTATCAGC AGAAGCCCGGTAAAGCCCCTAAGCTG CTGATCTACTGGGCCTCTACTAGAGA ATCAGGCGTGCCCTCTAGGTTTAGCG GTAGCGGTAGTGGCACCGACTTCACC TTCACTATCTCTAGCCTGCAGCCCGA GGATATCGCTACCTACTACTGTCAGA ACGACTATAGCTACCCCTACACCTTC GGTCAAGGCACTAAGGTCGAGATTAA G |
| SEQ ID NO: 18 | LC | EIVLTQSPATLSLSPGERATLSCKSSQS LLDSGNQKNFLTWYQQKPGKAPKLLIY WASTRESGVPSRFSGSGSGTDFTFTIS SLQPEDIATYYCQNDYSYPYTFGQGTK VEIKRTVAAPSVFIFPPSDEQLKSGTAS VVCLLNNFYPREAKVQWKVDNALQSG NSQESVTEQDSKDSTYSLSSTLTLSKA DYEKHKVYACEVTHQGLSSPVTKSFNR GEC |
| SEQ ID NO: 19 | DNA LC | GAGATCGTCCTGACTCAGTCACCCGC TACCCTGAGCCTGAGCCCTGGCGAGC GGGCTACACTGAGCTGTAAATCTAGT CAGTCACTGCTGGATAGCGGTAATCA GAAGAACTTCCTGACCTGGTATCAGC AGAAGCCCGGTAAAGCCCCTAAGCTG CTGATCTACTGGGCCTCTACTAGAGA ATCAGGCGTGCCCTCTAGGTTTAGCG GTAGCGGTAGTGGCACCGACTTCACC TTCACTATCTCTAGCCTGCAGCCCGA GGATATCGCTACCTACTACTGTCAGA ACGACTATAGCTACCCCTACACCTTC GGTCAAGGCACTAAGGTCGAGATTAA GCGTACGGTGGCCGCTCCCAGCGTG TTCATCTTCCCCCCCAGCGACGAGCA GCTGAAGAGCGGCACCGCCAGCGTG GTGTGCCTGCTGAACAACTTCTACCC |

TABLE A-continued

Amino acid and nucleotide sequences of exemplary anti-PD-1 antibody molecules

|  |  |  |
|---|---|---|
|  |  | CCGGGAGGCCAAGGTGCAGTGGAAG GTGGACAACGCCCTGCAGAGCGGCA ACAGCCAGGAGAGCGTCACCGAGCA GGACAGCAAGGACTCCACCTACAGCC TGAGCAGCACCCTGACCCTGAGCAAG GCCGACTACGAGAAGCATAAGGTGTA CGCCTGCGAGGTGACCCACCAGGGC CTGTCCAGCCCCGTGACCAAGAGCTT CAACAGGGGCGAGTGC |

BAP049-Clone-E HC

| SEQ ID NO: 1 (Kabat) | HCDR1 | TYWMH |
|---|---|---|
| SEQ ID NO: 2 (Kabat) | HCDR2 | NIYPGTGGSNFDEKFKN |
| SEQ ID NO: 3 (Kabat) | HCDR3 | WTTGTGAY |
| SEQ ID NO: 4 (Chothia) | HCDR1 | GYTFTTY |
| SEQ ID NO: 5 (Chothia) | HCDR2 | YPGTGG |
| SEQ ID NO: 3 (Chothia) | HCDR3 | WTTGTGAY |
| SEQ ID NO: 6 | VH | EVQLVQSGAEVKKPGESLRISCKGSGY TFTTYWMHWVRQATGQGLEWMGNIYP GTGGSNFDEKFKNRVTITADKSTSTAY MELSSLRSEDTAVYYCTRWTTGTGAY WGQGTTVTVSS |
| SEQ ID NO: 7 | DNA VH | GAGGTGCAGCTGGTGCAGTCAGGCG CCGAAGTGAAGAAGCCCGGCGAGTC ACTGAGAATTAGCTGTAAAGGTTCAG GCTACACCTTCACTACCTACTGGATG CACTGGGTCCGCCAGGCTACCGGTCA AGGCCTCGAGTGGATGGGTAATATCT ACCCCGGCACCGGCGGCTCTAACTTC GACGAGAAGTTTAAGAATAGAGTGAC TATCACCGCCGATAAGTCTACTAGCA CCGCCTATATGGAACTGTCTAGCCTG AGATCAGAGGACACCGCCGTCTACTA CTGCACTAGGTGGACTACCGGCACAG GCGCCTACTGGGGTCAAGGCACTACC GTGACCGTGTCTAGC |
| SEQ ID NO: 8 | HC | EVQLVQSGAEVKKPGESLRISCKGSGY TFTTYWMHWVRQATGQGLEWMGNIYP GTGGSNFDEKFKNRVTITADKSTSTAY MELSSLRSEDTAVYYCTRWTTGTGAY WGQGTTVTVSSASTKGPSVFPLAPCSR STSESTAALGCLVKDYFPEPVTVSWNS GALTSGVHTFPAVLQSSGLYSLSSVVTV PSSSLGTKTYTCNVDHKPSNTKVDKRV ESKYGPPCPPCPAPEFLGGPSVFLFPP KPKDTLMISRTPEVTCVVVDVSQEDPE VQFNWYVDGVEVHNAKTKPREEQFNS TYRVVSVLTVLHQDWLNGKEYKCKVSN KGLPSSIEKTISKAKGQPREPQVYTLPP SQEEMTKNQVSLTCLVKGFYPSDIAVE WESNGQPENNYKTTPPVLDSDGSFFLY SRLTVDKSRWQEGNVFSCSVMHEALH NHYTQKSLSLSLG |
| SEQ ID NO: 9 | DNA HC | GAGGTGCAGCTGGTGCAGTCAGGCG CCGAAGTGAAGAAGCCCGGCGAGTC ACTGAGAATTAGCTGTAAAGGTTCAG GCTACACCTTCACTACCTACTGGATG CACTGGGTCCGCCAGGCTACCGGTCA AGGCCTCGAGTGGATGGGTAATATCT ACCCCGGCACCGGCGGCTCTAACTTC GACGAGAAGTTTAAGAATAGAGTGAC TATCACCGCCGATAAGTCTACTAGCA CCGCCTATATGGAACTGTCTAGCCTG AGATCAGAGGACACCGCCGTCTACTA CTGCACTAGGTGGACTACCGGCACAG GCGCCTACTGGGGTCAAGGCACTACC GTGACCGTGTCTAGCGCTAGCACTAA |

TABLE A-continued

Amino acid and nucleotide sequences
of exemplary anti-PD-1 antibody molecules

GGGCCCGTCCGTGTTCCCCCTGGCA
CCTTGTAGCCGGAGCACTAGCGAATC
CACCGCTGCCCTCGGCTGCCTGGTCA
AGGATTACTTCCCGGAGCCCGTGACC
GTGTCCTGGAACAGCGGAGCCCTGAC
CTCCGGAGTGCACACCTTCCCCGCTG
TGCTGCAGAGCTCCGGGCTGTACTCG
CTGTCGTCGGTGGTCACGGTGCCTTC
ATCTAGCCTGGGTACCAAGACCTACA
CTTGCAACGTGGACCACAAGCCTTCC
AACACTAAGGTGGACAAGCGCGTCGA
ATCGAAGTACGGCCCACCGTGCCCGC
CTTGTCCCGCGCCGGAGTTCCTCGGC
GGTCCCTCGGTCTTTCTGTTCCCACC
GAAGCCCAAGGACACTTTGATGATTT
CCCGCACCCCTGAAGTGACATGCGTG
GTCGTGGACGTGTCACAGGAAGATCC
GGAGGTGCAGTTCAATTGGTACGTGG
ATGGCGTCGAGGTGCACAACGCCAAA
ACCAAGCCGAGGGAGGAGCAGTTCAA
CTCCACTTACCGCGTCGTGTCCGTGC
TGACGGTGCTGCATCAGGACTGGCTG
AACGGGAAGGAGTACAAGTGCAAAGT
GTCCAACAAGGGACTTCCTAGCTCAA
TCGAAAAGACCATCTCGAAAGCCAAG
GGACAGCCCCGGGAACCCCAAGTGT
ATACCCTGCCACCGAGCCAGGAAGAA
ATGACTAAGAACCAAGTCTCATTGACT
TGCCTTGTGAAGGGCTTCTACCCATC
GGATATCGCCGTGGAATGGGAGTCCA
ACGGCCAGCCGGAAAACAACTACAAG
ACCACCCCTCCGGTGCTGGACTCAGA
CGGATCCTTCTTCCTCTACTCGCGGC
TGACCGTGGATAAGAGCAGATGGCAG
GAGGGAAATGTGTTCAGCTGTTCTGT
GATGCATGAAGCCCTGCACAACCACT
ACACTCAGAAGTCCCTGTCCCTCTCC
CTGGGA

BAP049-Clone-E LC

| SEQ ID NO: 10 (Kabat) | LCDR1 | KSSQSLLDSGNQKNFLT |
| SEQ ID NO: 11 (Kabat) | LCDR2 | WASTRES |
| SEQ ID NO: 12 (Kabat) | LCDR3 | QNDYSYPYT |
| SEQ ID NO: 13 (Chothia) | LCDR1 | SQSLLDSGNQKNF |
| SEQ ID NO: 14 (Chothia) | LCDR2 | WAS |
| SEQ ID NO: 15 (Chothia) | LCDR3 | DYSYPY |
| SEQ ID NO: 20 | VL | EIVLTQSPATLSLSPGERATLSCKSSQS LLDSGNQKNFLTWYQQKPGQAPRLLIY WASTRESGVPSRFSGSGSGTDFTFTIS SLEAEDAATYYCQNDYSYPYTFGQGTK VEIK |
| SEQ ID NO: 21 | DNA VL | GAGATCGTCCTGACTCAGTCACCCGC TACCCTGAGCCTGAGCCCTGGCGAGC GGGCTACACTGAGCTGTAAATCTAGT CAGTCACTGCTGGATAGCGGTAATCA GAAGAACTTCCTGACCTGGTATCAGC AGAAGCCCGGTCAAGCCCCTAGACTG CTGATCTACTGGGCCTCTACTAGAGA ATCAGGCGTGCCCTCTAGGTTTAGCG GTAGCGGTAGTGGCACCGACTTCACC TTCACTATCTCTAGCCTGGAAGCCGA GGACGCCGCTACCTACTACTGTCAGA ACGACTATAGCTACCCCTACACCTTC GGTCAAGGCACTAAGGTCGAGATTAA G |
| SEQ ID NO: 22 | LC | EIVLTQSPATLSLSPGERATLSCKSSQS LLDSGNQKNFLTWYQQKPGQAPRLLIY WASTRESGVPSRFSGSGSGTDFTFTIS |

TABLE A-continued

Amino acid and nucleotide sequences of exemplary anti-PD-1 antibody molecules

| | | |
|---|---|---|
| | | SLEAEDAATYYCQNDYSYPYTFGQGTK VEIKRTVAAPSVFIFPPSDEQLKSGTAS VVCLLNNFYPREAKVQWKVDNALQSG NSQESVTEQDSKDSTYSLSSTLTLSKA DYEKHKVYACEVTHQGLSSPVTKSFNR GEC |
| SEQ ID NO: 23 | DNA LC | GAGATCGTCCTGACTCAGTCACCCGC TACCCTGAGCCTGAGCCCTGGCGAGC GGGCTACACTGAGCTGTAAATCTAGT CAGTCACTGCTGGATAGCGGTAATCA GAAGAACTTCCTGACCTGGTATCAGC AGAAGCCCGGTCAAGCCCCTAGACTG CTGATCTACTGGGCCTCTACTAGAGA ATCAGGCGTGCCCTCTAGGTTTAGCG GTAGCGGTAGTGGCACCGACTTCACC TTCACTATCTCTAGCCTGGAAGCCGA GGACGCCGCTACCTACTACTGTCAGA ACGACTATAGCTACCCCTACACCTTC GGTCAAGGCACTAAGGTCGAGATTAA GCGTACGGTGGCCGCTCCCAGCGTG TTCATCTTCCCCCCCAGCGACGAGCA GCTGAAGAGCGGCACCGCCAGCGTG GTGTGCCTGCTGAACAACTTCTACCC CCGGGAGGCCAAGGTGCAGTGGAAG GTGGACAACGCCCTGCAGAGCGGCA ACAGCCAGGAGAGCGTCACCGAGCA GGACAGCAAGGACTCCACCTACAGCC TGAGCAGCACCCTGACCCTGAGCAAG GCCGACTACGAGAAGCATAAGGTGTA CGCCTGCGAGGTGACCCACCAGGGC CTGTCCAGCCCCGTGACCAAGAGCTT CAACAGGGGCGAGTGC |
| BAP049-Clone-B HC | | |
| SEQ ID NO: 24 (Kabat) | HCDR1 | ACCTACTGGATGCAC |
| SEQ ID NO: 25 (Kabat) | HCDR2 | AATATCTACCCCGGCACCGGCGGCTC TAACTTCGACGAGAAGTTTAAGAAT |
| SEQ ID NO: 26 (Kabat) | HCDR3 | TGGACTACCGGCACAGGCGCCTAC |
| SEQ ID NO: 27 (Chothia) | HCDR1 | GGCTACACCTTCACTACCTAC |
| SEQ ID NO: 28 (Chothia) | HCDR2 | TACCCCGGCACCGGCGGC |
| SEQ ID NO: 26 (Chothia) | HCDR3 | TGGACTACCGGCACAGGCGCCTAC |
| BAP049-Clone-B LC | | |
| SEQ ID NO: 29 (Kabat) | LCDR1 | AAATCTAGTCAGTCACTGCTGGATAG CGGTAATCAGAAGAACTTCCTGACC |
| SEQ ID NO: 30 (Kabat) | LCDR2 | TGGGCCTCTACTAGAGAATCA |
| SEQ ID NO: 31 (Kabat) | LCDR3 | CAGAACGACTATAGCTACCCCTACAC C |
| SEQ ID NO: 32 (Chothia) | LCDR1 | AGTCAGTCACTGCTGGATAGCGGTAA TCAGAAGAACTTC |
| SEQ ID NO: 33 (Chothia) | LCDR2 | TGGGCCTCT |
| SEQ ID NO: 34 (Chothia) | LCDR3 | GACTATAGCTACCCCTAC |
| BAP049-Clone-E HC | | |
| SEQ ID NO: 24 (Kabat) | HCDR1 | ACCTACTGGATGCAC |
| SEQ ID NO: 25 (Kabat) | HCDR2 | AATATCTACCCCGGCACCGGCGGCTC TAACTTCGACGAGAAGTTTAAGAAT |
| SEQ ID NO: 26 (Kabat) | HCDR3 | TGGACTACCGGCACAGGCGCCTAC |
| SEQ ID NO: 27 (Chothia) | HCDR1 | GGCTACACCTTCACTACCTAC |

TABLE A-continued

Amino acid and nucleotide sequences of exemplary anti-PD-1 antibody molecules

| | | | |
|---|---|---|---|
| SEQ ID NO: 28 | (Chothia) | HCDR2 | TACCCCGGCACCGGCGGC |
| SEQ ID NO: 26 | (Chothia) | HCDR3 | TGGACTACCGGCACAGGCGCCTAC |

BAP049-Clone-E LC

| | | | |
|---|---|---|---|
| SEQ ID NO: 29 | (Kabat) | LCDR1 | AAATCTAGTCAGTCACTGCTGGATAGCGGTAATCAGAAGAACTTCCTGACC |
| SEQ ID NO: 30 | (Kabat) | LCDR2 | TGGGCCTCTACTAGAGAATCA |
| SEQ ID NO: 31 | (Kabat) | LCDR3 | CAGAACGACTATAGCTACCCCTACACC |
| SEQ ID NO: 32 | (Chothia) | LCDR1 | AGTCAGTCACTGCTGGATAGCGGTAATCAGAAGAACTTC |
| SEQ ID NO: 33 | (Chothia) | LCDR2 | TGGGCCTCT |
| SEQ ID NO: 34 | (Chothia) | LCDR3 | GACTATAGCTACCCCTAC |

Other Exemplary PD-1 Inhibitors

In one embodiment, the anti-PD-1 antibody molecule is Nivolumab (Bristol-Myers Squibb), also known as MDX-1106, MDX-1106-04, ONO-4538, BMS-936558, or OPDIVO®. Nivolumab (clone 5C4) and other anti-PD-1 antibodies are disclosed in U.S. Pat. No. 8,008,449 and WO 2006/121168, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Nivolumab, e.g., as disclosed in Table B.

In one embodiment, the anti-PD-1 antibody molecule is Pembrolizumab (Merck & Co), also known as Lambrolizumab, MK-3475, MK03475, SCH-900475, or KEYTRUDA®. Pembrolizumab and other anti-PD-1 antibodies are disclosed in Hamid, O. et al. (2013) *New England Journal of Medicine* 369 (2): 134-44, U.S. Pat. No. 8,354,509, and WO 2009/114335, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pembrolizumab, e.g., as disclosed in Table B.

In one embodiment, the anti-PD-1 antibody molecule is Pidilizumab (CureTech), also known as CT-011. Pidilizumab and other anti-PD-1 antibodies are disclosed in Rosenblatt, J. et al. (2011) *J Immunotherapy* 34(5): 409-18, U.S. Pat. Nos. 7,695,715, 7,332,582, and 8,686,119, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of Pidilizumab, e.g., as disclosed in Table B.

In one embodiment, the anti-PD-1 antibody molecule is MEDI0680 (Medimmune), also known as AMP-514. MEDI0680 and other anti-PD-1 antibodies are disclosed in U.S. Pat. No. 9,205,148 and WO 2012/145493, incorporated by reference in their entirety. In one embodiment, the anti-PD-1 antibody molecule comprises one or more of the CDR sequences (or collectively all of the CDR sequences), the heavy chain or light chain variable region sequence, or the heavy chain or light chain sequence of MEDI0680.

Further known anti-PD-1 antibodies include those described, e.g., in WO 2015/112800, WO 2016/092419, WO 2015/085847, WO 2014/179664, WO 2014/194302, WO 2014/209804, WO 2015/200119, U.S. Pat. Nos. 8,735,553, 7,488,802, 8,927,697, 8,993,731, and 9,102,727, incorporated by reference in their entirety.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signaling pathway, e.g., as described in U.S. Pat. No. 8,907,053, incorporated by reference in its entirety. In one embodiment, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In one embodiment, the PD-1 inhibitor is AMP-224 (B7-DCIg (Amplimmune), e.g., disclosed in WO 2010/027827 and WO 2011/066342, incorporated by reference in their entirety).

TABLE B

Amino acid sequences of other exemplary anti-PD-1 antibody molecules

Nivolumab

| | | |
|---|---|---|
| SEQ ID NO: 35 | HC | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |

TABLE B-continued

Amino acid sequences of other exemplary anti-PD-1 antibody molecules

| | | |
|---|---|---|
| SEQ ID NO: 36 | LC | EIVLTQSPATLSLSPGERATLSCRASQS VSSYLAWYQQKPGQAPRLLIYDASNRA TGIPARFSGSGSGTDFTLTISSLEPEDF AVYYCQQSSNWPRTFGQGTKVEIKRTV AAPSVFIFPPSDEQLKSGTASVVCLLNN FYPREAKVQWKVDNALQSGNSQESVT EQDSKDSTYSLSSTLTLSKADYEKHKVY ACEVTHQGLSSPVTKSFNRGEC |
| Pembrolizumab | | |
| SEQ ID NO: 37 | HC | QVQLVQSGVEVKKPGASVKVSCKASG YTFTNYYMYWVRQAPGQGLEWMGGIN PSNGGTNFNEKFKNRVTLTTDSSTTTA YMELKSLQFDDTAVYYCARRDYRFDM GFDYWGQGTTVTVSSASTKGPSVFPLA PCSRSTSESTAALGCLVKDYFPEPVTV SWNSGALTSGVHTFPAVLQSSGLYSLS SVVTVPSSSLGTKTYTCNVDHKPSNTK VDKRVESKYGPPCPPCPAPEFLGGPSV FLFPPKPKDTLMISRTPEVTCVVVDVSQ EDPEVQFNWYVDGVEVHNAKTKPREE QFNSTYRVVSVLTVLHQDWLNGKEYKC KVSNKGLPSSIEKTISKAKGQPREPQVY TLPPSQEEMTKNQVSLTCLVKGFYPSDI AVEWESNGQPENNYKTTPPVLDSDGS FFLYSRLTVDKSRWQEGNVFSCSVMH EALHNHYTQKSLSLSLGK |
| SEQ ID NO: 38 | LC | EIVLTQSPATLSLSPGERATLSCRASKG VSTSGYSYLHWYQQKPGQAPRLLIYLA SYLESGVPARFSGSGSGTDFTLTISSLE PEDFAVYYCQHSRDLPLTFGGGTKVEI KRTVAAPSVFIFPPSDEQLKSGTASVVC LLNNFYPREAKVQWKVDNALQSGNSQ ESVTEQDSKDSTYSLSSTLTLSKADYEK HKVYACEVTHQGLSSPVTKSFNRGEC |
| Pidilizumab | | |
| SEQ ID NO: 39 | HC | QVQLVQSGSELKKPGASVKISCKASGY TFTNYGMNWVRQAPGQGLQWMGWIN TDSGESTYAEEFKGRFVFSLDTSVNTA YLQITSLTAEDTGMYFCVRVGYDALDY WGQGTLVTVSSASTKGPSVFPLAPSSK STSGGTAALGCLVKDYFPEPVTVSWNS GALTSGVHTFPAVLQSSGLYSLSSVVTV PSSSLGTQTYICNVNHKPSNTKVDKRV EPKSCDKTHTCPPCPAPELLGGPSVFL FPPKPKDTLMISRTPEVTCVVVDVSHED PEVKFNWYVDGVEVHNAKTKPREEQY NSTYRVVSVLTVLHQDWLNGKEYKCKV SNKALPAPIEKTISKAKGQPREPQVYTL PPSREEMTKNQVSLTCLVKGFYPSDIAV EWESNGQPENNYKTTPPVLDSDGSFFL YSKLTVDKSRWQQGNVFSCSVMHEAL HNHYTQKSLSLSPGK |
| SEQ ID NO: 40 | LC | EIVLTQSPSSLSASVGDRVTITCSARSS VSYMHWFQQKPGKAPKLWIYRTSNLAS GVPSRFSGSGSGTSYCLTINSLQPEDF ATYYCQQRSSFPLTFGGGTKLEIKRTVA APSVFIFPPSDEQLKSGTASVVCLLNNF YPREAKVQWKVDNALQSGNSQESVTE QDSKDSTYSLSSTLTLSKADYEKHKVYA CEVTHQGLSSPVTKSFNRGEC |

Example of anti PD-L1 Antibody Molecule

In one embodiment, the combination product comprises a compound of Formula (I) or a pharmaceutically acceptable salt or co-crystal thereof, and an anti-PD-L1 antibody molecule such as those described herein.

Programmed Death Ligand 1 (PD-L1) has been described as a ligand for the immunoinhibitory receptor Programmed Death 1 (PD-1). Binding of PD-L1 to PD-1 leads to the inhibition of T cell receptor-mediated lymphocyte proliferation and cytokine secretion (Freeman et al. (2000) *J Exp Med* 192:1027-34). Thus, blocking of PD-L1 can lead to enhancement of antitumor immunity.

Several cell types express PD-L1. For example, PD-L1 is expressed on activated T cells, dendritic cells (DCs), natural killer (NK) cells, macrophages, B cells, monocytes, and vascular endothelium cells. PD-L1 is expressed in many cancers, including human lung, ovarian and colon carcinoma and various myelomas, (Iwai et al. (2002) *PNAS* 99:12293-7; Ohigashi et al. (2005) *Clin Cancer Res* 11:2947-53; Okazaki et al. (2007) *Intern. Immun.* 19:813-24; Thompson et al. (2006) *Cancer Res.* 66:3381-5). PD-L1 expression strongly correlates with unfavorable prognosis in various types of cancer including kidney, ovarian, bladder, breast, gastric and pancreatic cancer.

Many tumor infiltrating T lymphocytes predominantly express PD-1 compared to T lymphocytes in normal tissues and peripheral blood T lymphocytes. This indicates that up-regulation of PD-1 on tumor-reactive T cells can contribute to impaired antitumor immune responses (Ahmadzadeh et al. (2009) Blood 114:1537-44). Thus, PD-L1 signaling mediated by PD-L1 expressing tumor cells interacting with PD-1 expressing T cells may lead to attenuation of T cell activation and evasion of immune surveillance (Sharpe et al. (2002) *Nat Rev lmmunol.* 2:116-26; Keir et al. (2008) *Annu Rev lmmunol.* 26:677-704). PD-1 blockade can inhibit hematogenous spread of poorly immunogenic tumor cells by enhanced recruitment of effector T cells (Iwai et al. (2005) *Int. lmmunol.* 17:133-144).

Anti-PD-L1 can enhance T-cell immunity, e.g., through blocking both its inhibitory interactions with PD-1 and B7-1. Anti-PD-1 can also allow for immune regulation via PD-L2/PD-1. Both PD-1 and B7-1 are expressed on T cells, B cells, DCs, and macrophages, which provides potential for bidirectional interactions between B7-1 and PD-L1 on these cell types. PD-L1 on non-hematopoietic cells may interact with B7-1 as well as PD-1 on T cells.

In some embodiments, the anti-PD-L1 antibody molecule is chosen from YW243.55.570, MPDL3280A, MEDI-4736, MSB-0010718C, or MDX-1105.

In some embodiments, the anti-PD-L1 antibody is MSB0010718C. MSB0010718C (also referred to as A09-246-2; Merck Serono) is a monoclonal antibody that binds to PD-L1. MSB0010718C and other humanized anti-PD-L1 antibodies are disclosed in WO2013/079174, and having a sequence disclosed herein (or a sequence substantially identical or similar thereto, e.g., a sequence at least 85%, 90%, 95% identical or higher to the sequence specified). The heavy and light chain amino acid sequences of MSB0010718C include at least the following:

Heavy chain (SEQ ID NO: 24 as disclosed in WO2013/079174)
(SEQ ID NO: 42)
EVQLLESGGGLVQPGGSLRLSCAASGFTFSSYIMMWVRQAPGKGLEW

VSSIYPSGGITFYADKGRFTISRDNSKNTLYLQMNSLRAEDTAVYYC

ARIKLGTVTTVDYWGQGTLVTVSS

Light chain (SEQ ID NO: 25 as disclosed in WO2013/079174)
(SEQ ID NO: 43)
QSALTQPASVSGSPGQSITISCTGTSSDVGGYNYVSWYQQHPGKAPK

LMIYDVSNRPSGVSNRFSGSKSGNTASLTISGLQAEDEADYYCSSYT

SSSTRVFGTGTKVTVL

In one embodiment, the PD-L1 inhibitor is YW243.55.S70. The YW243.55.S70 antibody is an anti-PD-L1 described in WO 2010/077634 (heavy and light chain variable region sequences shown in SEQ ID NOs. 20 and 21, respectively), and having a sequence disclosed therein (or a sequence substantially identical or similar thereto, e.g., a sequence at least 85%, 90%, 95% identical or higher to the sequence specified).

In one embodiment, the PD-L1 inhibitor is MDX-1105. MDX-1105, also known as BMS-936559, is an anti-PD-L1 antibody described in WO2007/005874, and having a sequence disclosed therein (or a sequence substantially identical or similar thereto, e.g., a sequence at least 85%, 90%, 95% identical or higher to the sequence specified).

In one embodiment, the PD-L1 inhibitor is MDPL3280A (Genentech/Roche). MDPL3280A is a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In another embodiment, the PD-L1 inhibitor is an anti-PD-L1 antibody molecule disclosed in US 2016/0108123, filed Oct. 13, 2015, entitled "Antibody Molecules to PD-L1 and Uses Thereof," incorporated by reference in its entirety.

In one embodiment, the anti-PD-L1 antibody molecule includes at least one or two heavy chain variable domains (optionally including a constant region), at least one or two light chain variable domains (optionally including a constant region), or both, comprising the amino acid sequence of any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three complementarity determining regions (CDRs) from a heavy chain variable region and/or a light chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum 11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O; or as described in Table 1 of US 2016/0108123, or encoded by the nucleotide sequence in Table 1 of US 2016/0108123; or a sequence substantially identical (e.g., at least 80%, 85%, 90%, 92%, 95%, 97%, 98%, 99% or higher identical) to any of the aforesaid sequences.

In yet another embodiment, the anti-PD-L1 antibody molecule includes at least one, two, or three CDRs (or collectively all of the CDRs) from a heavy chain variable region comprising an amino acid sequence shown in Table 1 of US 2016/0108123, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123.

In yet another embodiment, the anti-PD-L1 antibody molecule includes at least one, two, or three CDRs (or collectively all of the CDRs) from a light chain variable region comprising an amino acid sequence shown in Table 1 of US 2016/0108123, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123. In certain embodiments, the anti-PD-L1 antibody molecule includes a substitution in a light chain CDR, e.g., one or more substitutions in a CDR1, CDR2 and/or CDR3 of the light chain.

In another embodiment, the anti-PD-L1 antibody molecule includes at least one, two, three, four, five or six CDRs (or collectively all of the CDRs) from a heavy and light chain variable region comprising an amino acid sequence shown in Table 1, or encoded by a nucleotide sequence shown in Table 1 of US 2016/0108123. In one embodiment, one or more of the CDRs (or collectively all of the CDRs) have one, two, three, four, five, six or more changes, e.g., amino acid substitutions or deletions, relative to the amino acid sequence shown in Table 1 of US 2016/0108123, or encoded by a nucleotide sequence shown in Table 1 of US 2016/0108123.

In one embodiment, the anti-PD-L1 antibody molecule includes at least one, two or three CDRs or hypervariable loops from a heavy chain variable region of an antibody described herein, e.g., an antibody chosen from any of BAP058-hum01, BAP058-hum02, BAP058-hum03, BAP058-hum04, BAP058-hum05, BAP058-hum06, BAP058-hum07, BAP058-hum08, BAP058-hum09, BAP058-hum10, BAP058-hum11, BAP058-hum12, BAP058-hum13, BAP058-hum14, BAP058-hum15, BAP058-hum16, BAP058-hum17, BAP058-Clone-K, BAP058-Clone-L, BAP058-Clone-M, BAP058-Clone-N, or BAP058-Clone-O, according to the Kabat and Chothia definition (e.g., at least one, two, or three CDRs or hypervariable loops according to the Kabat and Chothia definition as set out in Table 1 of US 2016/0108123); or encoded by the nucleotide sequence in Table 1 of US 2016/0108123; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Table 1 of US 2016/0108123.

In one embodiment, the anti-PD-L1 antibody molecule can include VH CDR1 according to Kabat et al. ((1991), "Sequences of Proteins of Immunological Interest," 5th Ed. Public Health Service, National Institutes of Health, Bethesda, Md.) or VH hypervariable loop 1 according to Chothia et al. (1992) J. Mol. Biol. 227:799-817, or a combination thereof, e.g., as shown in Table 1 of US 2016/0108123. In one embodiment, the combination of Kabat and Chothia CDR of VH CDR1 comprises the amino acid sequence GYTFTSYWMY (SEQ ID NO: 63), or an amino acid sequence substantially identical thereto (e.g., having at least one amino acid alteration, but not more than two, three or four alterations (e.g., substitutions, deletions, or insertions, e.g., conservative substitutions)). The anti-PD- L1 antibody molecule can further include, e.g., VH CDRs 2-3 according to Kabat et al. and VL CDRs 1-3 according to Kabat et al., e.g., as shown in Table 1 of US 2016/0108123.

In a preferred embodiment, the anti PD-L1 antibody molecule for use in the invention comprises:

(a) a heavy chain variable region (VH) comprising a VHCDR1 amino acid sequence of SEQ ID NO: 47, a VHCDR2 amino acid sequence of SEQ ID NO: 48, and a VHCDR3 amino acid sequence of SEQ ID NO: 46; and a light chain variable region (VL) comprising a VLCDR1 amino acid sequence of SEQ ID NO: 52, a VLCDR2 amino acid sequence of SEQ ID NO: 53, and a VLCDR3 amino acid sequence of SEQ ID NO: 54;

(b) a VH comprising a VHCDR1 amino acid sequence of SEQ ID NO: 44; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51;

(c) a VH comprising a VHCDR1 amino acid sequence of SEQ ID NO: 63, a VHCDR2 amino acid sequence of SEQ ID NO: 48, and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54; or (d) a VH comprising a VHCDR1 amino acid sequence of SEQ ID NO: 63; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54.

In one aspect of the previous embodiment, the anti-PD-L1 antibody molecule for use in the invention comprises a heavy chain variable domain comprising the amino acid sequence of SEQ ID NO: 55 and a light chain variable domain comprising the amino acid sequence of SEQ ID NO: 58.

In one aspect of the previous embodiment, the anti-PD-L1 antibody molecule for use in the invention comprises a heavy chain comprising the amino acid sequence of SEQ ID NO: 62 and a light chain comprising the amino acid sequence of SEQ ID NO: 60.

TABLE C

Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

| BAP058-hum13-HC | | |
|---|---|---|
| SEQ ID NO: 63 (Chothia and Kabat combined) | HCDR1 | GYTFTSYWMY |
| SEQ ID NO: 44 (Kabat) | HCDR1 | SYWMY |
| SEQ ID NO: 45 (Kabat) | HCDR2 | RIDPNSGSTKYNEKFKN |
| SEQ ID NO: 46 (Kabat) | HCDR3 | DYRKGLYAMDY |
| SEQ ID NO: 47 (Chothia) | HCDR1 | GYTFTSY |
| SEQ ID NO: 48 (Chothia) | HCDR2 | DPNSGS |
| SEQ ID NO: 46 (Chothia) | HCDR3 | DYRKGLYAMDY |
| SEQ ID NO: 55 | VH | EVQLVQSGAEVKKPGATVKISCKVSGYTFT SYWMYWVRQARGQRLEWIGRIDPNSGSTK YNEKFKNRFTISRDNSKNTLYLQMNSLRAE DTAVYYCARDYRKGLYAMDYWGQGTTVTV SS |
| SEQ ID NO: 56 | DNA VH | GAGGTCCAGCTGGTACAGTCTGGGGCTG AGGTGAAGAAGCCTGGGGCTACAGTGAAA ATCTCCTGCAAGGTTTCTGGCTACACCTTC ACCAGTTACTGGATGTACTGGGTGCGACA GGCTCGTGGACAACGCCTTGAGTGGATAG GTAGGATTGATCCTAATAGTGGGAGTACT AAGTACAATGAGAAGTTCAAGAACAGATTC ACCATCTCCAGAGACAATTCCAAGAACAC GCTGTATCTTCAAATGAACAGCCTGAGAG CCGAGGACACGGCCGTGTATTACTGTGCA AGGGACTATAGAAAGGGGCTCTATGCTAT GGACTACTGGGGCCAGGGCACCACCGTG ACCGTGTCCTCC |
| SEQ ID NO: 62 | Heavy Chain | EVQLVQSGAEVKKPGATVKISCKVSGYTFT SYWMYWVRQARGQRLEWIGRIDPNSGSTK YNEKFKNRFTISRDNSKNTLYLQMNSLRAE DTAVYYCARDYRKGLYAMDYWGQGTTVTV SSASTKGPSVFPLAPCSRSTSESTAALGCLV KDYFPEPVTVSWNSGALTSGVHTFPAVLQS SGLYSLSSWTVPSSSLGTKTYTCNVDHKP |

TABLE C-continued

Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

| | | |
|---|---|---|
| | | SNTKVDKRVESKYGPPCPPCPAPEFLGGPS<br>VFLFPPKPKDTLMISRTPEVTCVVVDVSQED<br>PEVQFNWYVDGVEVHNAKTKPREEQFNST<br>YRVVSVLTVLHQDWLNGKEYKCKVSNKGLP<br>SSIEKTISKAKGQPREPQVYTLPPSQEEMTK<br>NQVSLTCLVKGFYPSDIAVEWESNGQPENN<br>YKTTPPVLDSDGSFFLYSRLTVDKSRWQEG<br>NVFSCSVMHEALHNHYTQKSLSLSLGK |
| SEQ ID NO: 57 | DNA Heavy Chain | GAGGTCCAGCTGGTACAGTCTGGGGCTG<br>AGGTGAAGAAGCCTGGGGCTACAGTGAAA<br>ATCTCCTGCAAGGTTTCTGGCTACACCTTC<br>ACCAGTTACTGGATGTACTGGGTGCGACA<br>GGCTCGTGGACAACGCCTTGAGTGGATAG<br>GTAGGATTGATCCTAATAGTGGGAGTACT<br>AAGTACAATGAGAAGTTCAAGAACAGATTC<br>ACCATCTCCAGAGACAATTCCAAGAACAC<br>GCTGTATCTTCAAATGAACAGCCTGAGAG<br>CCGAGGACACGGCCGTGTATTACTGTGCA<br>AGGGACTATAGAAAGGGGCTCTATGCTAT<br>GGACTACTGGGGCCAGGGCACCACCGTG<br>ACCGTGTCCTCCGCTTCCACCAAGGGCCC<br>ATCCGTCTTCCCCCTGGCGCCCTGCTCCA<br>GGAGCACCTCCGAGAGCACAGCCGCCCT<br>GGGCTGCCTGGTCAAGGACTACTTCCCCG<br>AACCGGTGACGGTGTCGTGGAACTCAGG<br>CGCCCTGACCAGCGGCGTGCACACCTTC<br>CCGGCTGTCCTACAGTCCTCAGGACTCTA<br>CTCCCTCAGCAGCGTGGTGACCGTGCCCT<br>CCAGCAGCTTGGGCACGAAGACCTACACC<br>TGCAACGTAGATCACAAGCCCAGCAACAC<br>CAAGGTGGACAAGAGAGTTGAGTCCAAAT<br>ATGGTCCCCCATGCCCACCGTGCCCAGCA<br>CCTGAGTTCCTGGGGGGACCATCAGTCTT<br>CCTGTTCCCCCCAAAACCCAAGGACACTC<br>TCATGATCTCCCGGACCCCTGAGGTCACG<br>TGCGTGGTGGTGGACGTGAGCCAGGAAG<br>ACCCCGAGGTCCAGTTCAACTGGTACGTG<br>GATGGCGTGGAGGTGCATAATGCCAAGAC<br>AAAGCCGCGGGAGGAGCAGTTCAACAGC<br>ACGTACCGTGTGGTCAGCGTCCTCACCGT<br>CCTGCACCAGGACTGGCTGAACGGCAAG<br>GAGTACAAGTGCAAGGTGTCCAACAAAGG<br>CCTCCCGTCCTCCATCGAGAAAACCATCT<br>CCAAAGCCAAAGGGCAGCCCCGAGAGCC<br>ACAGGTGTACACCCTGCCCCCATCCCAGG<br>AGGAGATGACCAAGAACCAGGTCAGCCTG<br>ACCTGCCTGGTCAAAGGCTTCTACCCCAG<br>CGACATCGCCGTGGAGTGGGAGAGCAAT<br>GGGCAGCCGGAGAACAACTACAAGACCA<br>CGCCTCCCGTGCTGGACTCCGACGGCTC<br>CTTCTTCCTCTACAGCAGGCTAACCGTGG<br>ACAAGAGCAGGTGGCAGGAGGGGAATGT<br>CTTCTCATGCTCCGTGATGCATGAGGCTC<br>TGCACAACCACTACACACAGAAGAGCCTC<br>TCCCTGTCTCTGGGTAAA |

BAP058-hum13-LC

| | | | |
|---|---|---|---|
| SEQ ID NO: 49 | (Kabat) | LCDR1 | KASQDVGTAVA |
| SEQ ID NO: 50 | (Kabat) | LCDR2 | WASTRHT |
| SEQ ID NO: 51 | (Kabat) | LCDR3 | QQYNSYPLT |
| SEQ ID NO: 52 | (Chothia) | LCDR1 | SQDVGTA |
| SEQ ID NO: 53 | (Chothia) | LCDR2 | WAS |
| SEQ ID NO: 54 | (Chothia) | LCDR3 | YNSYPL |

TABLE C-continued

Amino acid and nucleotide sequences for humanized anti-PD-L1 mAb BAP058-hum013. The amino acid and nucleotide sequences of the heavy and light chain CDRs, the heavy and light chain variable regions, and the heavy and light chains are shown.

| | | |
|---|---|---|
| SEQ ID NO: 58 | VL | AIQLTQSPSSLSASVGDRVTITCKASQDVGT AVAWYLQKPGQSPQLLIYWASTRHTGVPSR FSGSGSGTDFTFTISSLEAEDAATYYCQQY NSYPLTFGQGTKVEIK |
| SEQ ID NO: 59 | DNA VL | GCCATCCAGTTGACCCAGTCTCCATCCTC CCTGTCTGCATCTGTAGGAGACAGAGTCA CCATCACTTGCAAGGCCAGTCAGGATGTG GGTACTGCTGTAGCCTGGTACCTGCAGAA GCCAGGGCAGTCTCCACAGCTCCTGATCT ATTGGGCATCCACCCGGCACACTGGGGT CCCCTCGAGGTTCAGTGGCAGTGGATCTG GGACAGATTTCACCTTTACCATCAGTAGC CTGGAAGCTGAAGATGCTGCAACATATTA CTGTCAGCAGTATAACAGCTATCCTCTCAC GTTCGGCCAAGGGACCAAGGTGGAAATCA AA |
| SEQ ID NO: 60 | Light Chain | AIQLTQSPSSLSASVGDRVTITCKASQDVGT AVAWYLQKPGQSPQLLIYWASTRHTGVPSR FSGSGSGTDFTFTISSLEAEDAATYYCQQY NSYPLTFGQGTKVEIKRTVAAPSVFIFPPSD EQLKSGTASVVCLLNNFYPREAKVQWKVDN ALQSGNSQESVTEQDSKDSTYSLSSTLTLS KADYEKHKVYACEVTHQGLSSPVTKSFNRG EC |
| SEQ ID NO: 61 | DNA Light Chain | GCCATCCAGTTGACCCAGTCTCCATCCTC CCTGTCTGCATCTGTAGGAGACAGAGTCA CCATCACTTGCAAGGCCAGTCAGGATGTG GGTACTGCTGTAGCCTGGTACCTGCAGAA GCCAGGGCAGTCTCCACAGCTCCTGATCT ATTGGGCATCCACCCGGCACACTGGGGT CCCCTCGAGGTTCAGTGGCAGTGGATCTG GGACAGATTTCACCTTTACCATCAGTAGC CTGGAAGCTGAAGATGCTGCAACATATTA CTGTCAGCAGTATAACAGCTATCCTCTCAC GTTCGGCCAAGGGACCAAGGTGGAAATCA AACGTACGGTGGCTGCACCATCTGTCTTC ATCTTCCCGCCATCTGATGAGCAGTTGAA ATCTGGAACTGCCTCTGTTGTGTGCCTGC TGAATAACTTCTATCCCAGAGAGGCCAAA GTACAGTGGAAGGTGGATAACGCCCTCCA ATCGGGTAACTCCCAGGAGAGTGTCACAG AGCAGGACAGCAAGGACAGCACCTACAG CCTCAGCAGCACCCTGACGCTGAGCAAAG CAGACTACGAGAAACACAAAGTCTACGCC TGCGAAGTCACCCATCAGGGCCTGAGCTC GCCCGTCACAAAGAGCTTCAACAGGGGA GAGTGT |

Dosage and Administration of the Immunotherapeutic Agent

The immunotherapeutic agent (Such as an anti-PD-1 antibody molecule or an anti-PD-L1 molecule antibody) can be administered to the subject systemically (e.g., orally, parenterally, subcutaneously, intravenously, rectally, intramuscularly, intraperitoneally, intranasally, transdermally, or by inhalation or intracavitary installation), topically, or by application to mucous membranes, such as the nose, throat and bronchial tubes.

Dosages and therapeutic regimens of the immunotherapeutic agent (e.g.anti-PD-1 antibody molecule or anti PD-L1 antibody molecule) can be determined by a skilled artisan. In certain embodiments, the immunotherapeutic agent (e.g. anti-PD-1 antibody molecule) is administered by injection (e.g., subcutaneously or intravenously) at a dose of about 1 to 30 mg/kg, e.g., about 5 to 25 mg/kg, about 10 to 20 mg/kg, about 1 to 5 mg/kg, or about 3 mg/kg. The dosing schedule can vary from e.g., once a week to once every 2, 3, or 4 weeks. In one embodiment, the anti-PD-1 antibody molecule is administered at a dose from about 10 to 20 mg/kg every other week. In another embodiment, the anti-PD-1 antibody molecule is administered at a dose from about 1 to 10 mg/Kg, or from about 1 to 5 mg/Kg or about 3 mg/kg every 4 weeks.

For example, the anti-PD-1 antibody molecule is administered or used at a flat or fixed dose. In some embodiments, the anti-PD-1 antibody molecule is administered by injection (e.g., subcutaneously or intravenously) at a dose (e.g., a flat dose) of about 200 mg to 500 mg, e.g., about 250 mg to 450 mg, about 300 mg to 400 mg, about 250 mg to 350 mg, about 350 mg to 450 mg, or about 300 mg or about 400 mg. The dosing schedule (e.g., flat dosing schedule) can vary from e.g., once a week to once every 2, 3, 4, 5, or 6 weeks.

In one embodiment, the anti-PD-1 antibody molecule is administered at a dose from about 300 mg to 400 mg once every three weeks or once every four weeks. In one embodiment, the anti-PD-1 antibody molecule is administered at a dose from about 300 mg once every three weeks. In one embodiment, the anti-PD-1 antibody molecule is administered at a dose from about 400 mg once every four weeks. In one embodiment, the anti-PD-1 antibody molecule is administered at a dose from about 300 mg once every four weeks. In one embodiment, the anti-PD-1 antibody molecule is administered at a dose from about 400 mg once every three weeks.

In another embodiment, the anti-PD-1 antibody molecule is administered at a flat dose of about 300 mg to 400 mg once every three weeks or once every four weeks. In a subset of this embodiment, the anti-PD-1 antibody molecule is administered at a flat dose of about 400 mg every four weeks. In yet another subset of this embodiment, the anti-PD-1 antibody molecule is administered at a flat dose of about 300 mg every three weeks.

EXAMPLES

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The invention is illustrated, but in no way limited, by the following Examples.

Abbreviations
ACN acetonitrile
aq aqueous
br broad
BSA bovine serum albumin
CPBA: 3-chlorobenzoperoxoic acid
d doublet
dd doublet of doublets
DCM dichloromethane
DMF N,N-dimethylformamide
DMSO dimethylsulfoxide
EtOAc ethyl acetate
g grams
h hour(s)
HPLC high performance liquid chromatography
IS internal standard
LCMS liquid chromatography coupled to mass spectrometry
M molar
m multiplet
MeOH methanol
min minutes
mL milliliter(s)
mmol millimoles
MS mass spectrometry
m/z mass to charge ratio
NADPH beta-nicotinamide dinucleotide phosphate, reduced form
NMR nuclear magnetic resonance
ppm parts per million
rt room temperature
$R_t$ retention time
s singlet
sat saturated
t triplet
THF tetrahydrofuran
UPLC Methods:

UPLC 2 min: Waters UPLC Acquity; column: Acquity HSS T3, 1.8 mm, 2.1*50 mm, at 60° C., Eluent A: water+0.05% HCOOH+3.75 mM ammonium acetate, B: ACN+0.04% HCOOH, Gradient: 5 to 98% B in 1.4 min, Flow: 1.0 mL/min.

UPLC 10 min : Waters UPLC Acquity; column: Acquity HSS T3, 1.8 mm, 2.1*50 mm, at 60° C., Eluent A: water+0.05% HCOOH+3.75 mM ammonium acetate, B: ACN+0.04% HCOOH, Gradient: 5 to 98% B in 9.4 min hold 0.4 min, Flow: 1 mL/min.)

Example 1: Preparation of 1-(4-amino-5-bromo-6-(1H-pyrazol-1-yl)pyrimidin-2-yl)-1H-pyrazol-4-ol

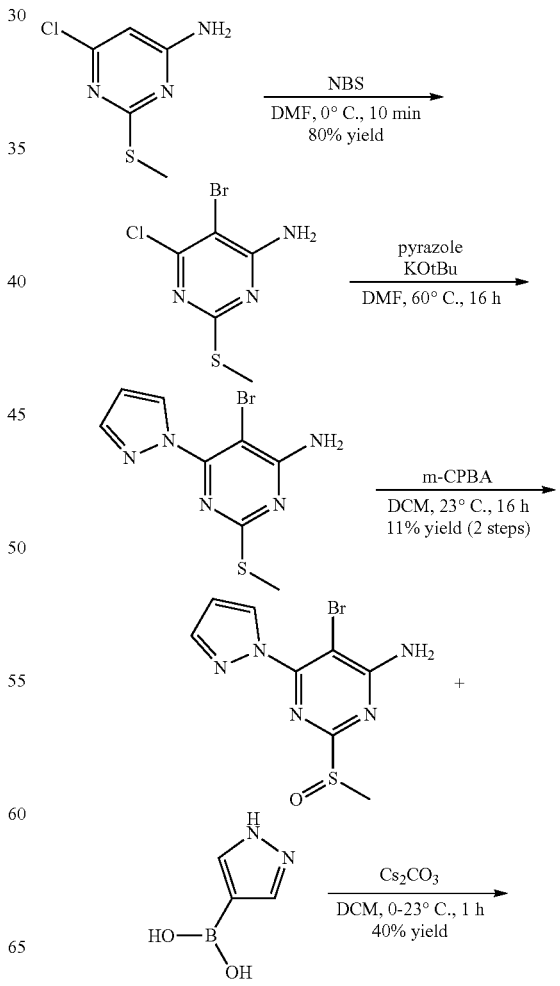

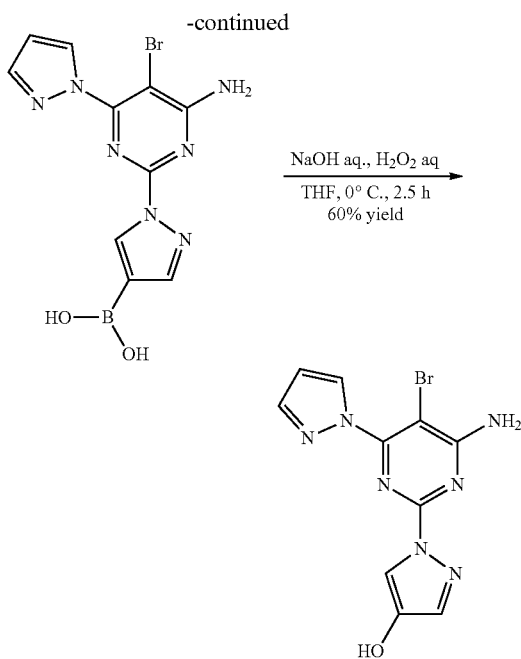

5-Bromo-6-chloro-2-(methylthio)pyrimidin-4-amine

To a cooled solution of 6-chloro-2-(methylthio)pyrimidin-4-amine (15.0 g, 85 mmol) in DMF (150 ml) was added N-bromosuccinimide (16.7 g, 94 mmol) portionwise with stirring at 0° C. After 10 min the reaction was quenched by the addition of water at 0° C. The reaction mixture was diluted with brine and extracted 3 times with EtOAc. The combined organic phases were washed twice with saturated aqueous NaHCO$_3$ solution, then brine, separated, and filtered through a phase separator with Na$_2$SO$_4$ to dry. The filtrate was concentrated in vacuo to give the title compound (18.8 g, 74 mmol, 80% yield, 92% purity) as colorless solid which was used in the next step without further purification. M/z=254/256/258 [M+H]+, Rt=0.95 min (UPLC 2 min), 1H NMR (600 MHz, DMSO-d6) δ 8.03 (br s, 1H), 7.25 (br s, 1H), 2.42 (s, 3H).

5-Bromo-2-(methylthio)-6-(1H-pyrazol-1-yl)pyrimidin-4-amine

A mixture of 5-bromo-6-chloro-2-(methylthio)pyrimidin-4-amine (17.8 g, 70 mmol), 1H-pyrazole (4.7 g, 69 mmol), and KOtBu (7.9 g, 70 mmol) in DMF (250 mL) was stirred at 60° C. for 16 hours. The solvent was reduced in vacuo and the residue was diltued with saturated aqueous NaHCO$_3$ solution and extracted 3 times with EtOAc. The combined organic phases were washed with brine, separated, and filtered through a phase separator with Na$_2$SO$_4$ to dry. The filtrate was concentrated in vacuo to give the title compound (20 g, 64% purity) which was used in the next step without further purification. M/z=286/288/290 [M+H]+, Rt=0.85 min (U PLC 2 min), 1H NMR (600 MHz, DMSO-d6) δ 8.35 (d, J=2.5 Hz, 1H), 8.03 (br s, 1H), 7.81 (br s, 1H), 7.26 (br s, 1H), 6.55 (s, 1H), 2.46 (s, 3H).

5-Bromo-2-(methylsulfinyl)-6-(1H-pyrazol-1-yl)pyrimidin-4-amine

To a suspension of 5-bromo-2-(methylthio)-6-(1H-pyrazol-1-yl)pyrimidin-4-amine (20 g, 64% purity) in DCM (100 mL) was added a solution of 3-chlorobenzoperoxoic acid (9.3 g, 53.7 mmol) in DCM (100 mL) dropwise with stirring over 20 min at 0° C. and the resulting mixture was stirred at 23° C. for 16 hours. The reaction mixture was filtered to collect the precipitate and washed with DCM. The solid was dried in vacuo to give the title compound (2.4 g, 7.6 mmol, 11% yield over two steps) as colorless solid. M/z=302/304 [M+H]+, Rt=0.53 min (UPLC 2 min), 1H NMR (600 MHz, DMSO-d6) δ 8.63 (br s, 1H), 8.38 (d, J=2.3 Hz, 1H), 7.87 (s, 1H), 7.72 (s, 1H), 6.60-6.61 (m, 1H), 2.86 (s, 3H).

(1-(4-amino-5-bromo-6-(1H-pyrazol-1-yl)pyrimidin-2-yl)-1H-pyrazol-4-yl)boronic acid To a mixture of 5-bromo-2-(methylsulfinyl)-6-(1H-pyrazol-1-yl)pyrimidin-4-amine (50 mg, 0.17 mmol) and (1H-pyrazol-4-yl)boronic acid (18 mg, 0.17 mmol) in DMF (1 ml) was added Cs$_2$CO$_3$ (54 mg, 0.17 mmol) at 0° C. The resulting mixture was stirred for 1 hour at 23° C. The reaction mixture was diluted with water and extracted 3 times with EtOAc. The combined organic phases were washed with water then brine, separated, and filtered through a phase separator with Na$_2$SO$_4$ to dry. The filtrate was concentrated in vacuo to give the title compound (30 mg, 0.066 mmol, 40% yield) which was used in the next step without further purification. M/z=350/352 [M+H]+, Rt=0.55 min (UPLC 2 min).

1-(4-amino-5-bromo-6-(1H-pyrazol-1-yl)pyrimidin-2-yl)-1H-pyrazol-4-ol

To a vigorously stirred solution of (1-(4-amino-5-bromo-6-(1H-pyrazol-1-yl)pyrimidin-2-yl)-1H-pyrazol-4-yl)boronic acid (30 mg, 0.066 mmol) in THF (1 mL) were added 25wt % aqueous NaOH solution (0.021 mL, 0.13 mmol) and 30% aqueous H$_2$O$_2$ solution (0.020 mL, 0.20 mmol) at 0° C. After 30 minutes another 30% aqueous H$_2$O$_2$ solution (0.020 mL, 0.20 mmol) was added and the mixture was stirred at the same temperature for 2.5 hours in total. The reaction was quenched with saturated aqueous NH$_4$Cl solution then diluted with water, and extracted 4 times with DCM and 3 times with DCM/MeOH 4/1 mixture. The combined organic phases were filtered through a phase separator to dry and the filtrate was concentrated in vacuo. The crude product was absorbed onto isolute and purified by column chromatography (ISCO, 12 g-silica-redisep-column, flow: 30 ml/min, Solvent: CH$_2$Cl$_2$:MeOH from 1:0, hold for 3 min, then to 96:4 over 25 min). The product fractions were combined and concentrated in vacuo to give the title compound (14 mg, 0.040 mmol, 60% yield) as colorless solid. M/z=322/324 [M+H]+, Rt=0.58 min (UPLC 2 min); Rt=2.27 min; purity at 254 nm: >95% (UPLC 10 min), 1H NMR (600 MHz, DMSO-d6) δ 9.23 (br s, 1H), 8.44 (d, J=2.5 Hz, 1H), 8.32 (br s, 1H), 7.94 (s, 1H), 7.90-7.81 (m, 1H), 7.46 (br s, 2H), 6.63-6.50 (m, 1H).

Alernatively, 6-chloro-2-(methylthio)pyrimidin-4-amine could be reacted first with pyrazole in the presence of a base, to generate 2-(methylthio)-6-(1H-pyrazol-1-yl)pyrimidin-4-amine; followed by treatment with NBS to generate 5-Bromo-2-(methylthio)-6-(1H-pyrazol-1-yl)pyrimidin-4-amine.

Example 1A: Preparation of 1-(6-amino-5-bromo-2-(1H-pvrazol-1-yl)pyrimidin-4-yl)-1H-pvrazol-4-ol

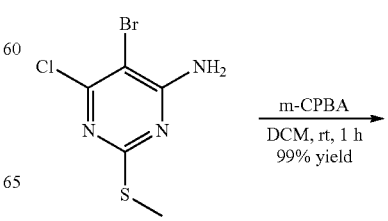

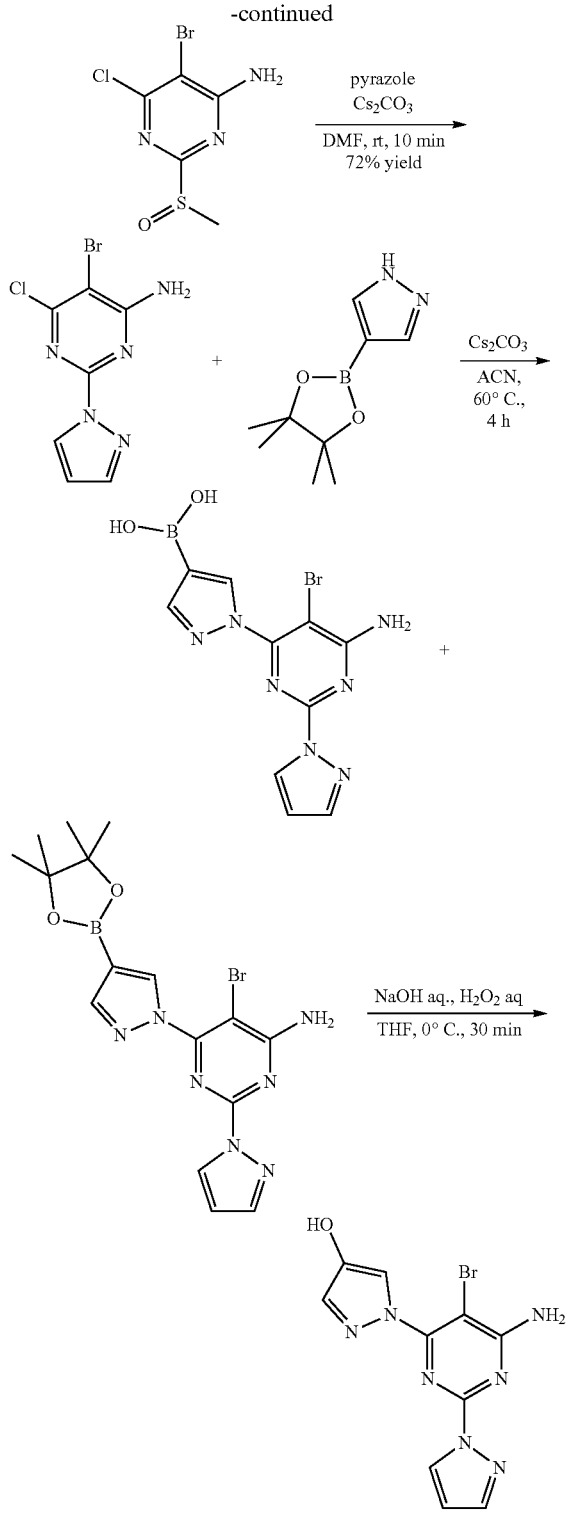

5-bromo-6-chloro-2-(methylsulfinyl)pyrimidin-4-amine

To a solution of 5-bromo-6-chloro-2-(methylthio)pyrimidine-4-amine 13 g (52 mmol) in 450 ml of DCM, 13 g (57 mmol) of m-chloroperbenzoic acid (77%) (Sigma-Aldrich) dissolved in 100 ml of DCM was added slowly dropwise. The solution was stirred at room temperature for 1 hour. The white precipitate formed was filtered, washed several times with DCM and dried. There were obtained 14 g (99%) of the title compound. M/z=270/272 [M+H]+, Rt=0.56 min (UPLC 2 min), 1H-NMR (400 MHz, DMSO-d6) δ 8.17 (d, 2H), 2.78 (s, 3H).

5-bromo-6-chloro-2-(1H-pyrazol-1-yl)pyrimidin-4-amine 2 g (7.4 mmol) of 5-bromo-6-chloro-2-(methylsulfinyl)pyrimidine-4-amine was suspended in 30 ml of DMF. To this suspension was added 0.5 g (7.4 mmol) of 1H-pyrazole and 1.5 g (4.4 mmol) of cesium carbonate. The reaction mixture was strongly stirred at room temperature for 10 min. The solution was poured onto 200 ml of cool water. The formed precipitate was filtered, washed with cool water and dried. The desired product is obtained as white solid (1.5 g, 72%). M/z32 274/276 [M+H]+, Rt=0.80 min (UPLC 2 min), 1H-NMR (400 MHz, DMSO-d6) δ 8.44 (d, 1H), 8.15 (d, 2H), 7.81 (d, 1H), 6.56 (dd, 1H).

(1-(6-amino-5-bromo-2-(1H-pyrazol-1-yl)pyrimidin-4-yl)-1H-pyrazol-4-yl)boronic acid A mixture of 0.10 g (0.36 mmol) of 5-bromo-6-chloro-2-(1H-pyrazol-1-yl)pyrimidin-4-amine, 0.14 g (0.73 mmol) of 4-(4,4,5,5-tetramethyl-1,3,2-dioxaborolan-2-yl)-1H-pyrazole and 0.12 g (0.36 mmol) of cesium carbonate in 10 ml of acetonitrile was stirred for 4 h at 60° C. in a sealed glass tube. Then the solvent was removed by reduced pressure. The solid obtained was washed with ether/pentane and dried. The mixture of boronic acid and boronic ester was used in the next step without further purification.

1-(6-amino-5-bromo-2-(1H-pyrazol-1-yl)pyrimidin-4-yl)-1H-pyrazol-4-ol

To a solution of (1-(6-amino-5-bromo-2-(1H-pyrazol-1-yl)pyrimidin-4-yl)-1H-pyrazol-4-yl)boronic acid or 5-bromo-2-(1H-pyrazol-1-yl)-6-(4-(4,4,5,5-tetramethyl-1,3,2-dioxaborolan-2-yl)-1H-pyrazol-1-yl)pyrimidin-4-amine in THF (2.5 ml), cooled to 0° C., was added 2 ml of NaOH 1N and $H_2O_2$ (30%) (0.23 ml, 2.32 mmol). The mixture was stirred at room temperature for 30 min. The reaction was acidified to pH 3-4 by addition of HCl 1N, extracted with ethyl acetate and dried over anhydrous $Na_2SO_4$, and concentrated in vacuum. The crude product was purified by silica gel column chromatography using DCM-MeOH (2-5%). M/z=322/324 [M+H]+, Rt=0.58 min (UPLC 2 min); 1H NMR (600 MHz, DMSO-d6) δ 9.18 (br s, 1H), 8.57-8.78 (m, 1H), 8.29 (br s, 1H), 7.97 (s, 1H), 7.79 (s, 1H), 7.54 (s, 1H), 7.40 (br s, 1H), 6.55 (s, 1H).

Example 2—Isolation/Characterization of the Metabolite of 5-bromo-2,6-di(1H-pyrazol-1-yl)pyrimidin-4-amine: In Vitro Metabolite Identification in Rat, Dog and Human Microsomes Using Liquid Chromatography and Mass Spectrometry Abbreviations:
ACN: acetonitrile
CC: calibration curve
IS: internal standard
DMSO: dimethylsulfoxide
MRM: multiple reaction monitoring
NADH: nicotinamide adenine dinucleotide phosphate (reduced)
Rpm: revolution per minute
Liver Microsomes
Rat liver microsomes (male, pooled, Sprague Dawley)
Source: XenoTech, LLC (Kansas, USA)
Protein content: 20 mg/mL
Catalogue number: R I 000, Lot number: 0710623
Dog liver microsomes (male, pooled, Beagle)
Source: XenoTech, LLC (Kansas, USA)

Protein content: 20 mg|mL
Catalogue number: D I 000, Lot number: 0810143
Human liver microsomes (mixed gender, pooled)
Source: XenoTech, LLC (Kansas, USA)
Protein content: 20 mg|mL
Catalogue number: H061 0, Lot number: 101042
Stock Solutions and Reagents
Test Item A 2 mM and 0.2 mM stock solution of 5-bromo-2,6-di(1H-pyrazol-1-yl)pyrimindin-4-amine was prepared in DMSO for in vitro incubations. The final organic content in liver microsomal incubations was 0.5%.

A 2.5 mM stock solution of 1-(6-amino-5-bromo-2-(1H-pyrazol-1-yl)-pyrimidin-4-yl)-1H-pyrazol-4-ol and 1-(4-amino-5-bromo-6-(1H-pyrazol-1-yl)-pyrimidin-4-yl)-1H-pyrazol-6-ol were prepared separetly in DMSO. The stock solutions were further diluted in acetonitrile to obtain 1 uM concentration of 1-(6-amino-2-bromo-6-(1H-pyrazol-1-yl)-pyrimidin-4-yl)-1H-pyrazol-4-ol and 1-(4-amino-5-bromo-6-(1H-pyrazol-1-yl)-pyrimidin-4-yl)-1H-pyrazol-6-ol for chromatographyic runs.

A 0.1 mM stock solution of diclofenac and verapamil was prepared in DMSO for in vitro incubations. The final organic content in liver microsomal incubations was 0.5%.

In Vitro Microsomal Incubations

Liver microsomal protein (25 uL for 0.5 mg/mL; 15 uL for 0.3 mg/mL), NADPH (100 uL, 2 mM final concentration) and phosphate buffer (870 uL for 0.5 mg/mL; 880 uL for 0.3 mg/mL) were incubated in a microfuge tube in an orbital shaker incubator for 10 min maintained at 37° C. Reactions were initiated by spiking 5 uL of 2 mM and 0.2 mM 5-bromo-2,6-di(1H-pyrazol-1-yl)pyrimindin-4-amine(10 uM final concentrations for 0.5 mg/mL protein; 1 uM final concentration for 0.3 mg/mL protein; 0.5% final DMSO concentration) and samples incubated at 37° C. Aliquots (200 uL) were withdrawn from the reaction tube at 0, 60 and 120 minutes and the reaction was quenched by addition of 100 uL acetonitrile. Reactions were performed in duplicates. The quenched samples were centrifuged at 14000 rpm (approximately 21000 g) for 10 minutes(Eppendorf Centrifuge 5810 R) and supernatant was analyzed by LCMS/MS.

Control incubations (no NADPH added) and blank incubations (no test item added) were performed in singlet for each species. These samples were withdrawn at 0 and 120 min and quenched using acetonitrile. The supernatant was analyzed for any non microsomal degradation and matrix interference. Diclofenac in rat and human liver microsomes and verapamil in dog liver microsomes was used as a positive control. Reaction and control experiments were performed in singlet. Diclofenac and verapamil metabolic turnover data was matching with in-house historical data.

Analytical Methods and Instrumentation Conditions

Samples were processed using protein precipitation method and then analyzed by employing linear gradient with a run time of 28 min in HPLC coupled with tandem mass spectrometry (API 4000 mass spectrometer). Each sample was injected and scanned separately for Q1 (MH+/MH−) and MS/MS.

The different possible metabolite peaks were identified in Q1 scan after assessing for matrix interference using test item free blank samples, and were confirmed from the fragmentation pattern (MSIMS scan). The summary of analytical method is presented in table 9.

TABLE 9

Chromatographic and mass spectrometry conditions

Chromatographic conditions:

| | |
|---|---|
| Column | Kromasil C18, 150 × 4.6 mm, 5 um (Chromatographic service) |
| Injection Volume | 10 uL |
| Flow rate | 900 uL/min 28 min |
| Run time | |
| Sample cooler temperature | 6° C. |
| Colum oven temperature | 40° C. |

| | Time (min) | 5 mM Ammonium Formate (0.05% Formic acid) 80% + 20% ACN | 5 mM Ammonium Formate (0.05% Formic acid) 20% + 80% ACN |
|---|---|---|---|
| Linear Gradient | 0.01 | 95 | 5 |
| | 5 | 95 | 5 |
| | 23 | 5 | 95 |
| | 24 | 95 | 5 |
| | 28 | 95 | 5 |

Mass spectrometric condition:

| | | | |
|---|---|---|---|
| Instrument | | API 4000 LC-MS/MS | |
| Scanning Modes | Q1 | MS/MS | |
| Scanning range/Product ion | 100 to 1000 amu | 308 | 324 |
| Declustering potential | 60 | 60 | 60 |
| Entrance potential | 10 | 10 | 10 |
| Collision energy | — | 35 | 35 |
| Ionisation Mode | +ve | +ve | +ve |
| Collision gas | — | 6 | 6 |
| Curtain gas | 20 | 15 | 15 |
| Ion source gas 1 | 40 | 30 | 30 |
| Ion source gas 2 | 50 | 60 | 60 |
| Ion Spray voltage | 5500 | 5500 | 5500 |
| Temperature | 500 | 500 | 500 |

Modified Analytical Method:

An alternate analytical method was also developed to increase the retention times and to assess other metabolites apart from the identified M-1 metabolite. Aqueous solutions of 1-(6-amino-5-bromo-2-(1H-pyrazol-1-yl)pyrimidin-4-yl)-1H-pyrazol-4-ol and 1-(4-amino-5-bromo-6-(1H-pyrazol-1-yl)pyrimidin-2-yl)-1H-pyrazol-4-ol (1 uM) were co-chromatographed with the in vitro incubated samples employing modified analytical method to confirm the identity. The summary of modified method is presented in table 10.

TABLE 10

Modified Chromatographic and mass spectrometry conditions

Chromatographic conditions:

| | |
|---|---|
| Column | Kromasil C18, 150 × 4.6 mm, 5 um (Chromatographic service) |
| Injection Volume | 10 uL |
| Flow rate | 600 uL/min 28 min |
| Run time | |
| Sample cooler temperature | 6° C. |
| Colum oven temperature | 40° C. |

TABLE 10-continued

Modified Chromatographic and mass spectrometry conditions

| | Time (min) | 0.1% Formic acid in water | 0.1% Formic acid in ACN |
|---|---|---|---|
| Linear Gradient | 0.01 | 95 | 5 |
| | 5 | 95 | 5 |
| | 23 | 5 | 95 |
| | 24 | 95 | 5 |
| | 28 | 95 | 5 |

Mass spectrometric condition:

| Instrument | API 4000 LC-MS/MS | | |
|---|---|---|---|
| Scanning Modes | Q1 | MS/MS | |
| Scanning range/Product ion | 100 to 1000 amu | 308 | 324 |
| Declustering potential | 60 | 60 | 60 |
| Entrance potential | 10 | 10 | 10 |
| Collision energy | — | 35 | 35 |
| Ionisation Mode | +ve | +ve | +ve |
| Collision gas | — | 6 | 6 |
| Curtain gas | 20 | 15 | 15 |
| Ion source gas 1 | 40 | 30 | 30 |
| Ion source gas 2 | 50 | 60 | 60 |
| Ion Spray voltage | 5500 | 5500 | 5500 |
| Temperature | 500 | 500 | 500 |

Mass Balance Determination in Human Liver Microsomes

Stock solution of 5-bromo-2,6-di(1H-pyrazol-1-yl)pyrimindin-4-amine and 1-(4-amino-5-bromo-6-(1H-pyrazol-1-yl)pyrimidin-2-yl)-1H-pyrazol-4-ol were serialy diluted in DMSO to obtain spiking solution concentrations of 1, 0.5 and 0.25 mM and 0.5, 0.25 and 0.125 mM, respectively.

Calibration standards of 5-bromo-2,6-di(1H-pyrazol-1-yl)pyrimindin-4-amine and 1-(4-amino-5-bromo-6-(1H-pyrazol-1-yl)pyrimidin-2-yl)-1H-pyrazol-4-ol were prepared by spiking 5 uL of the respective spiking solutions in to 995 uL of incubation buffer to obtain 10, 5, 2.5 and 1.25 uM samples for 5-bromo-2,6-di(1H-pyrazol-1-yl)pyrimindin-4-amine and 5, 2.5, 1.25 and 0.625 uM samples for 1-(4-amino-5-bromo-6-(1H-pyrazol-1-yl)pyrimidin-2-yl)-1H-pyrazol-4-ol.

An aliquot of 200 uL of these spiked samples of 5-bromo-2,6-di(1H-pyrazol-1-yl)pyrimindin-4-amine and 1-(6-amino-5-bromo-2-(1H-pyrazol-1-yl)pyrimidin-4-yl)-1H-pyrazol-4-ol were diluted with 100 uL of acetonitrile. An aliquot (25 uL) of these samples were further diluted with 100 uL of internal standard (Haloperidol, 1 ug|mL in acetonitrile).

The incubation samples were also prepared similar to that of the calibration standards by adding 25 uL of the quenched sample with 100 uL of internal standard.

The incubation samples were then quantified independently for 5-bromo-2,6-di(1H-pyrazol-1-yl)pyrimindin-4-amine and 1-(4-amino-5-bromo-6-(1H-pyrazol-1-yl)pyrimidin-2-yl)-1H-pyrazol-4-ol in MRM mode and method details are presented in table 11.

TABLE 11

Chromatographic and mass spectrometry conditions-MRM analysis

Chromatographic conditions:

| Column | Gemini C18, 150 × 4.6 mm, 5 um (Phenomenex) |
|---|---|
| Injection Volume | 10 uL |
| Flow rate | 600 uL/min 3 min |
| Run time | |

TABLE 11-continued

Chromatographic and mass spectrometry conditions-MRM analysis

| Sample cooler temperature | 8° C. | | |
|---|---|---|---|
| Colum oven temperature | 40° C. | | |
| Mobile phase | Milli-Q water:methanol:ACN (10:30:60, v/v/v) with 0.1% liquor ammonia | | |

Mass spectrometric condition:

| Instrument | API 4000 LC-MS/MS | | |
|---|---|---|---|
| Compound | parent | metabolite | Haloperidol |
| MRM transition | 308.1/94.0 | 324.0/110.1 | 376.2/165.1 |
| Declustering potential | 70 | 70 | 50 |
| Entrance energy | 10 | 10 | 10 |
| Collision energy | 48 | 40 | 25 |
| Collision cell exit potential | 10 | 12 | 10 |
| Ionization mode | +ve | | |
| Collision gas | 6 | | |
| Curtain gas | 30 | | |
| Ion source gas 1 | 30 | | |
| Ion source gas 2 | 60 | | |
| Ion Spray voltage | 5500 | | |
| Temperature | 550 | | |
| Interface | ON | | |

Results

In vitro samples were assessed for the presence of metabolites.cThe MH+ (Q I) and product ions (MS/MS) at different retention times for the possible 5-bromo-2,6-di(1H-pyrazol-1-yl)pyrimindin-4-amine metabolites with fragmentation pattern are presented in Table 1 and below.

TABLE 1

Fragmentation patter for parent (5-bromo-2,6-di(1H-pyrazol-1-yl)pyrimidin-4-amine) and its metabolites

| Possible Transformation | Retention Time | MH+ | Prodcut ions |
|---|---|---|---|
| Parent | 10.36 | 308.0 | 308.0, 208.0, 240.1, 200.3, 147.0, 93.9 |
| Monooxygenation product | 6.22 | 324.2 | 324.2, 266.5, 239.9, 187.0, 161.3, 109.9 |

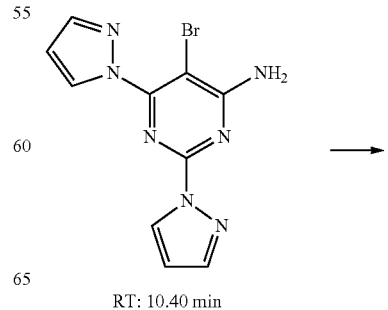

RT: 10.40 min

-continued

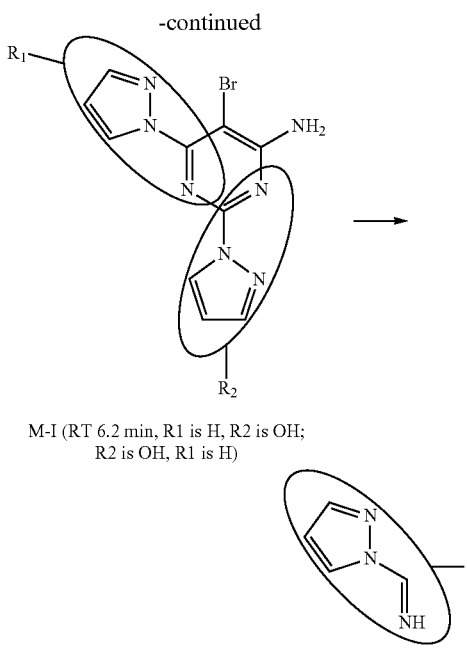

M-I (RT 6.2 min, R1 is H, R2 is OH;
R2 is OH, R1 is H)

A summary of these putative metabolites of 5-bromo-2,6-di(1H-pyrazol-1-yl)pyrimindin-4-amine detected across the different species is presented in Table 2.

TABLE 2

Summary of metabolites of 5-bromo-2,6-di(1H-pyrazol-1-yl)pyrimindin-4-amine detected

| Possible Transformation | Monooxygenation (M−1) | 5-bromo-2,6-di(1H-pyrazol-1-yl)pyrimindin-4-amine (M) |
|---|---|---|
| Retention time | 6.22 | 10.36 |
| MH+ | 324.2 | 308.0 |
| Rat liver microsomes | X | X |
| Dog liver microsomes | X | X |
| Human liver microsomes | X | X |

X indicates presence

Relative abundance of parent and its metabolite in microsomal samples is presented in Table 3.

TABLE 3

Relative abundance of 5-bromo-2,6-di(1H-pyrazol-1-yl)pyrimindin-4-amine (10 uM) and its metabolites detected in liver mircosomes using MRM anlysis

| Liver Micro-somes | Analyte Rep-licate | Percentage area ratio with respect to parent (10 uM) | | | | | |
|---|---|---|---|---|---|---|---|
| | | 0 min | | 60 min | | 120 min | |
| | | Set 1 | Set 2 | Set 1 | Set 2 | Set 1 | Set 2 |
| Rat | Parent | 100 | 100 | 100* | 74 | 100* | 52 |
| | M-I | ND | ND | 0.0 g | 0.06 | 0.13 | 0.14 |
| Dog | Parent | 100 | 100 | 84 | 94 | 88 | 100* |
| | M-I | 0.01 | 0.01 | 0.56 | 0.67 | 0.95 | 1.52 |
| Human | Parent | 100 | 100 | 94 | 85 | 84 | 74 |
| | M-I | 0.01 | 0.02 | 0.97 | 0.93 | 1.84 | 1.78 |

Parent is 5-bromo-2,6-di(1H-pyrazol-1-yl)pyrimindin-4-amine

ND: not detected; relative abundance of Parent and its metabolites are quantitative values; calculated by considering that ionization efficiency is similar for parent and its metabolites; *% remaining values greater than 100% were considered 100 for calculations.

Figure 2:
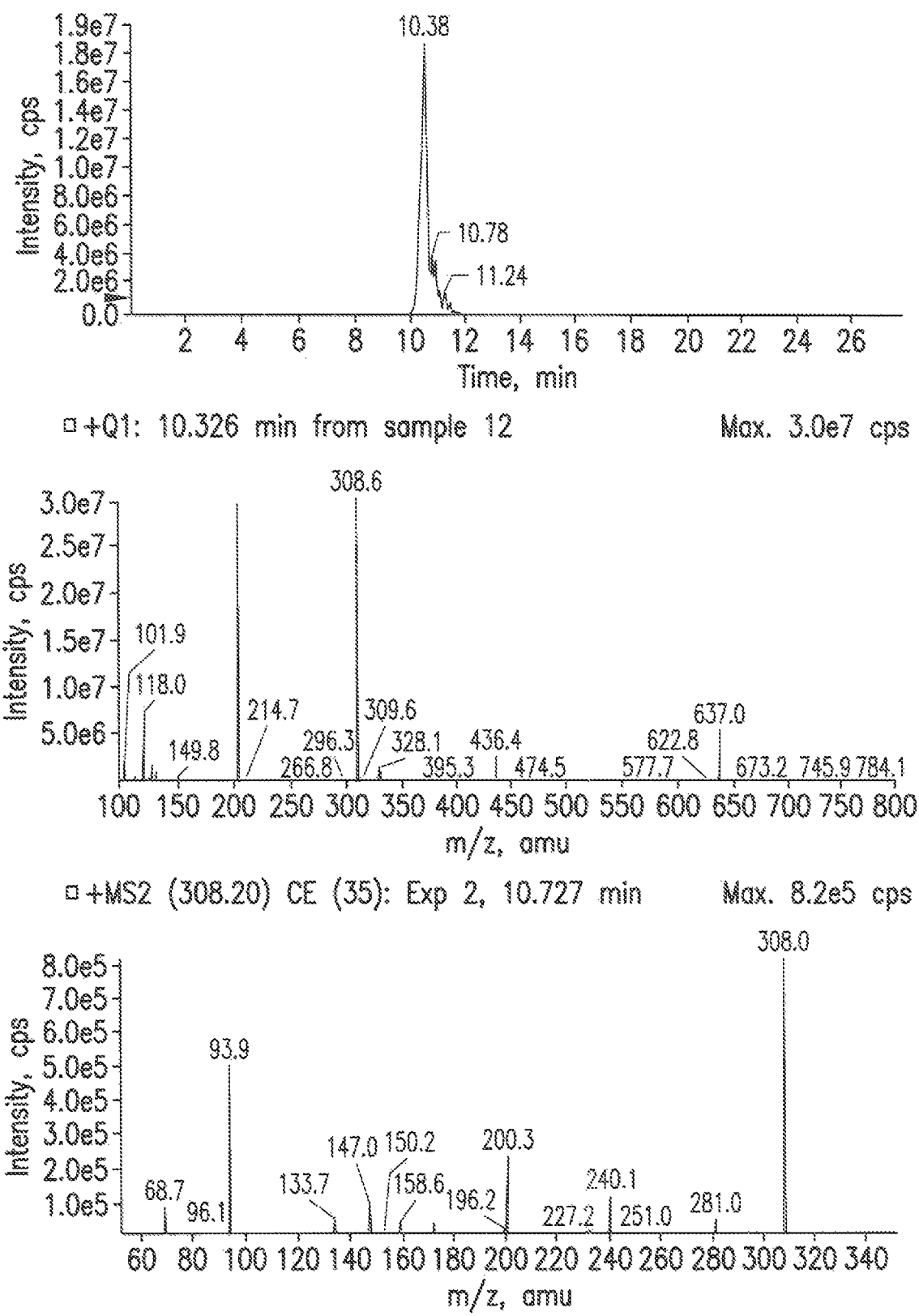
FIG. 2. Illustrates XIC chromatogram, Q1 and MS/MS spectrum of 5-bromo-2,6-di(1H-pyrazol-1-yl)pyrimindin-4-amine in human liver microsomes 120 minutes (MH+: 308).
Figure 3:
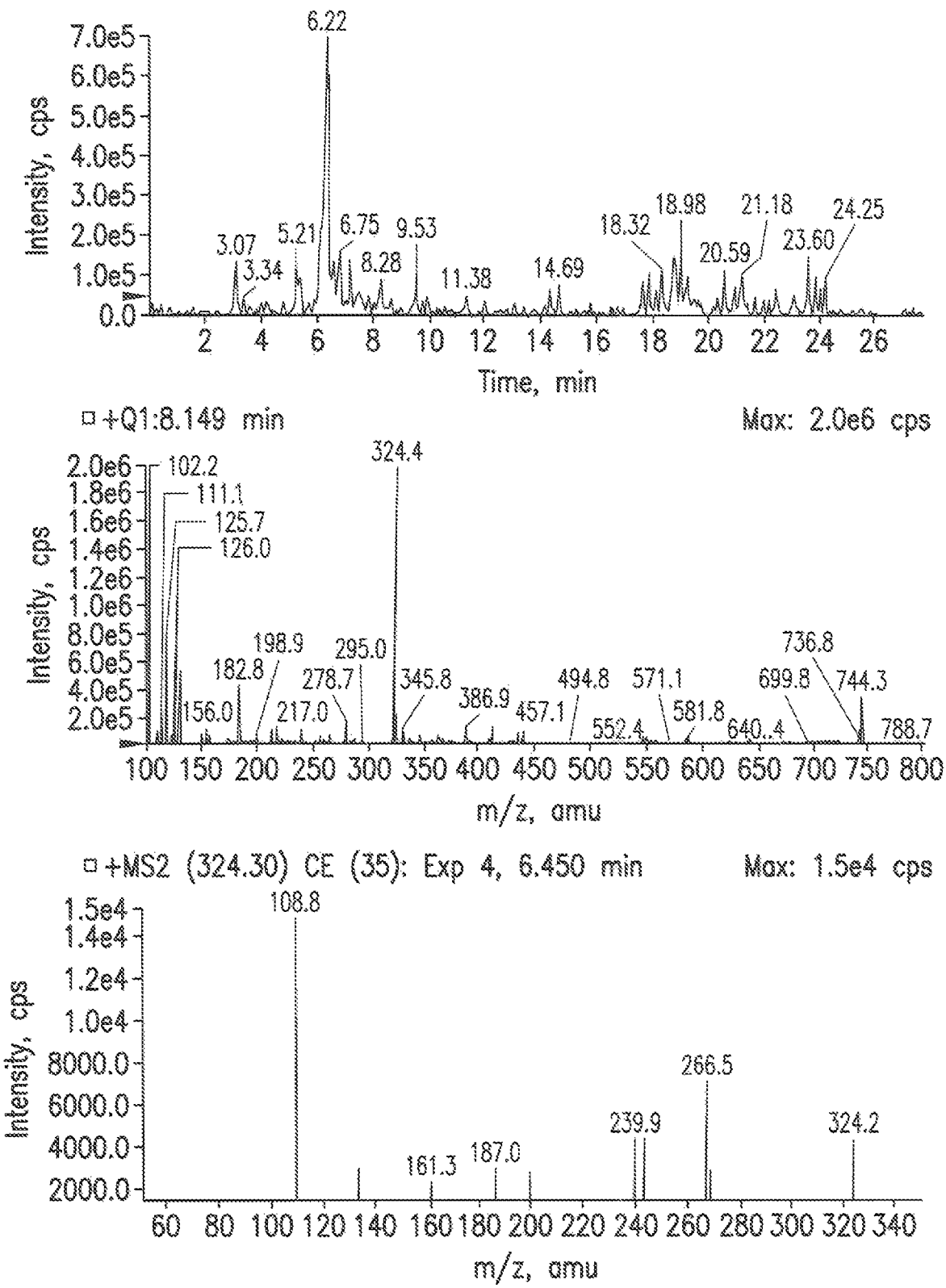
FIG. 3. Illustrates XIC chromatogram, Q1 and MS/MS spectrum of monooxygenated product of 5-bromo-2,6-di (1H-pyrazol-1-yl)pyrimindin-4-amine in human liver microsomes 120 minutes (MH+: 324)

Extracted ion chromatograms (XIC), Q1 and MS/MS spectra of aqueous standard and selected microsomal samples are presented in FIGS. 1 to 3.

A monooxygenation metabolite (M-I, 6.22 min) was produced in rat, dog and human liver microsomes. The percentage of metabolite with respect to parent (5-bromo-2,6-di(1H-pyrazol-1-yl)pyrimindin-4-amine) was uniformly low. However this analysis assumes equal ionization efficiency for both metabolite and parent compounds (Table 3).

Independently, time dependent loss of 5-bromo-2,6-di(1H-pyrazol-1-yl)pyrimindin-4-amine (1 uM), diclofenac (positive control for human and rat, 0.5 uM), verapamil (positive control for dog, 0.5 uM) in liver microsomes (0.3 mg/mL protein concentration) was studied. The results are presented in Table 4 and Table 5.

TABLE 4

Time-dependent loss of 5-bromo-2,6-di(1H-pyrazol-1-yl)pyrimindin-4-amine (1 uM) incubation in human, dog and rat liver microsomes (0.3 mg/mL)

| Experimental conditions | Time (minutes) | Human Liver Microsomes % remaining | | Dog Liver Microsomes % remaining | | Rat Liver Microsomes % remaining | |
|---|---|---|---|---|---|---|---|
| | | Set-1 | Set-2 | Set-1 | Set-2 | Set-1 | Set-2 |
| Reaction mixture containing NADPH | 0 | 100 | 100 | 100 | 100 | 100 | 100 |
| | 60 | 40 | 48 | 50 | 52 | 78 | 76 |
| | 120 | 24 | 22 | 17 | 17 | 65 | 52 |
| NADPH-free control | 0 | 100 | | 100 | | 100 | |
| | 120 | 97 | | 100 | | 100 | |
| Parent compound free Control (Blank) | 0 | No interference at the retention time of parent compound | | No interference at the retention time of parent compound | | No interference at the retention time of parent compound | |
| | 120 | | | | | | |

Parent compound is 5-bromo-2,6-di(1H-pyrazol-1-yl)pyrimindin-4-amine
% remaining values greater than 100% were considered 100 for calculations

TABLE 5

Time-Dependent loss of Positive controls (0.5 uM) incubation in liver microsomes (0.3 mg/mL)

| Liver microsomes | Time (minutes) | % remaining Human (Diclofenac) | % remaining Rat (diclofenac) | % remaining Dog (Verapamil) |
|---|---|---|---|---|
| Reaction mixture containing NADPH | 0 | 100 | 100 | 100 |
| | 60 | 100 | 12 | 9 |
| | 120 | 6 | 1 | 1 |
| NADPH-free control | 0 | 100 | 100 | 100 |
| | 120 | 98 | 100 | 94 |

The control incubations of 5-bromo-2,6-di(1H-pyrazol-1-yl)pyrimindin-4-amine (no NADPH added) was found stable up to 120 min, indicating no non-CYP mediated metabolism. Blank incubations (no test item added) did not show any matrix interference (Table 4).

The relative metabolism of 5-bromo-2,6-di(1H-pyrazol-1-yl)pyrimindin-4-amine at 1 uM concentrations and 0.3 mg/mL microsomal protein concentrations across tested species was DLM>HLM>RLM. The results are presented in Table 6.

TABLE 6

Relative metabolism of 5-bromo-2,6-di(1H-pyrazol-1-yl)pyrimindin-4-amine in different species

| Micro-somes | Final Concentration of parent (uM) | Final protein concentration (mg/mL) | % metabolism of parent at 120 min Set-1 | Set-2 | Concentration of Analyte metabolized (uM)* Set-1 | Set-2 |
|---|---|---|---|---|---|---|
| Rat | 10 | 0.5 | 0 | NA | 0 | NA |
| Dog | | | 12 | 6 | 1.2 | 0.6 |
| Human | | | 16 | 26 | 1.6 | 2.6 |
| Rat | 1 | 0.3 | 35 | 48 | 0.35 | 0.48 |
| Dog | | | 83 | 83 | 0.83 | 0.83 |
| Human | | | 76 | 78 | 0.76 | 0.78 |

*Concentration of analyte metabolized (uM) is calculated by using below Formula: Concentration of analyte Metabolized = (% metabolism at 120 min × Final concentration of parent compound)/100.

Parent compound is 5-bromo-2,6-di(1H-pyrazol-1-yl)pyrimindin-4-amine 1-(6-amino-5-bromo-2-(1H-pyrazol-1-yl)pyrimidin-4-yl)-1H-pyrazol-4-ol and 1-(4-amino-5-bromo-6-(1H-pyrazol-1-yl)pyrimidin-2-yl)-1H-pyrazol-4-ol were synthesized. The structures of these compounds are presented below.

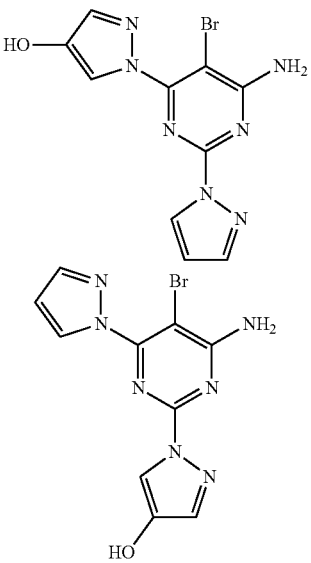

Figure 4:
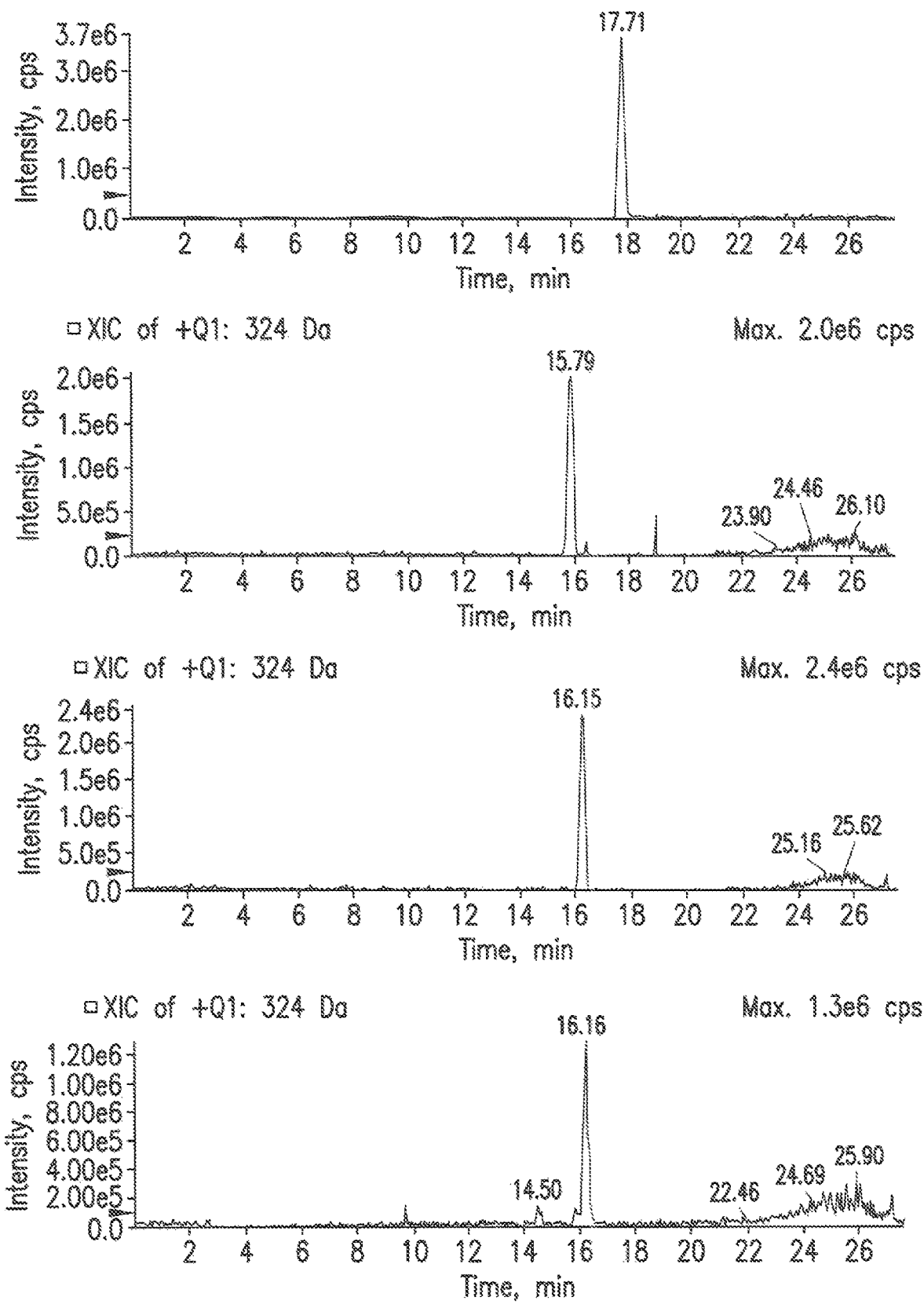
FIG. 4. illustrates Q1 spectrum of aqueous standards of 5-bromo-2,6-di(1H-pyrazol-1-yl)pyrimindin-4-amine (1 uM; MH+:308) and its monooxygenated products: 1-(6-amino-5-bromo-2-(1H-pyrazol-1-yl)-pyrimidin-4-yl)-1H-pyrazol-4-ol (1 uM; MH+: 324) and 1-(4-amino-5-bromo-6-(1H-pyrazol-1-yl)-pyrimidin-2-yl)-1H-pyrazol-4-ol (1 uM; MH+: 324) and identification of 1-(4-amino-5-bromo-6-(1H-pyrazol-1-yl)-pyrimidin-2-yl)-1H-pyrazol-4-ol in human liver microsomes 120 minutes (MH+: 324)

The identity of the metabolite detected in the human microsomal incubation samples were then determined by co-chromatography with compounds, 1-(6-amino-5-bromo-2-(1H-pyrazol-1-yl)pyrimidin-4-yl)-1H-pyrazol-4-ol and 1-(4-amino-5-bromo-6-(1H-pyrazol-1-yl)pyrimidin-2-yl)-1H-pyrazol-4-ol by monitoring in Q1 mode. The co-chromatography results confirmed the identity of the metabolite (M-I) detected in the microsomal samples as 1-(4-amino-5-bromo-6-(1H-pyrazol-1-yl)pyrimidin-2-yl)-1H-pyrazol-4-ol. The chromatogram is presented in the FIG. 4.

5-bromo-2,6-di(1H-pyrazol-1-yl)pyrimindin-4-amine and its metabolite (M-I, 1-(4-amino-5-bromo-6-(1H-pyrazol-1-yl)pyrimidin-2-yl)-1H-pyrazol-4-ol) were quantified in the incubated human liver microsomal samples in MRM mode using 4 point calibration curve standard. The percentage of M-I metabolite in human liver microsomes is about 15-20% after 60 minutes of incubation with parent. The mass balance of about 95 to 107% was achieved for the metabolism in human liver microsomes. The results are presented in Table 7. The calibration curve summary for 5-bromo-2,6-di(1H-pyrazol-1-yl)pyrimindin-4-amine and 1-(4-amino-5-bromo-6-(1H-pyrazol-1-yl)pyrimidin-2-yl)-1H-pyrazol-4-ol is presented in Table 8.

TABLE 7

Mass balance of 5-bromo-2,6-di(1H-pyrazol-1-yl)pyrimindin-4-amine metabolism in human liver microsomes using MRM analysis % metabolite formation and Mass balance of Parent (10 uM) in Human liver microsomes

| | Time (min) | Parent Concentration (uM) | M-I Concentration (uM) | % parent Remaining | % M-I detected | Mass balance |
|---|---|---|---|---|---|---|
| Set-1 | 0 | 11.78$^a$ | 0 | 100 | 0 | NA |
| | 30 | 11.34$^a$ | 1.29 | 96.26 | 10.95 | 107.22 |
| | 60 | 10.47$^a$ | 2.23 | 88 | 18.93 | 107.81 |
| Set-2 | 0 | 11.54$^a$ | 0 | 100 | 0 | NA |
| | 30 | 10.09$^a$ | 0.92 | 87.44 | 7.97 | 95.41 |
| | 60 | 9.18 | 1.74 | 79.55 | 15.08 | 94.63 |

A Values are within 20% +/− of ULOQ (upper limit of quantification)

TABLE 8

Calibration curve summary of 5-bromo-2,6-di(1H-pyrazol-1-yl)pyrimindin-4-amine and 1-(4-amino-5-bromo-6-(1H-pyrazol-1-yl)pyrimidin-2-yl)-1H-pyrazol-4-ol in human liver microsomes

| Analyte | Standards | STD A | STD B | STD C | STD D | Slope | Intercept | Coeff. of determination ($r^2$) |
|---|---|---|---|---|---|---|---|---|
| Parent | Nominal Conc (uM) | 1.25 | 2.50 | 5.00 | 10.00 | | NA | |
| | Calc. Conc (uM) | 1.25 | 2.51 | 5.02 | 9.94 | 0.00409 | 0.0126 | 1.000 |
| | % accuracy | 99.79 | 100.34 | 100.44 | 99.42 | | | |

TABLE 8-continued

Calibration curve summary of 5-bromo-2,6-di(1H-pyrazol-1-yl)pyrimindin-4-amine and 1-(4-amino-5-bromo-6-(1H-pyrazol-1-yl)pyrimidin-2-yl)-1H-pyrazol-4-ol in human liver microsomes

| Analyte | Standards | STD A | STD B | STD C | STD D | Slope | Intercept | Coeff. of determination ($r^2$) |
|---|---|---|---|---|---|---|---|---|
| Metabolite | Nominal Conc (uM) | 0.63 | 1.25 | 2.50 | 5.00 | | NA | |
| | Calc. Conc (uM) | 0.63 | 1.22 | 2.64 | 4.82 | 0.0000189 | 0.000618 | 0.9981 |
| | % accuracy | 100.2 | 97.62 | 105.75 | 96.43 | | | |

The M-I metabolite formed in human liver microsomes accounts for 15-20% of the parent. The M-I metabolite formed in rat and dog is not determined quantitatively and therefore, formation of this metabolite may be higher or lower than in human liver microsomes.

In conclusion, 5-bromo-2,6-di(1H-pyrazol-1-yl)pyrimidin-4-amine is metabolized through oxidation pathway in thevtested preclinical species and human microsomes in vitro and the metabolitevdetected was identical to 1-(4-amino-5-bromo-6-(1H-pyrazol-1-yl)pyrimidin-2-yl)-1H-pyrazol-4-ol as confirmed chromatographically.

Example 3: In Vitro hA2A Radioligand Binding Assay

Compound binding affinity was determined by radioligand binding (RLB) competition assay using [3H]-ZM241385 (ARC, Cat # ART0884) as radioligand and membranes prepared from HEK-293 cells stably expressing the human adenosine A2A receptor (Perkin Elmer RBHA2AM400UA) using 50 mM Tris pH 7.5, 1 mM MgCl$_2$, 0.1 mg/ml BSA, 0.2 U/ml Adenosine Deaminase as assay buffer. Membranes were precoupled to Yttrium silicate (YSI) wheatgerm agglutinin (WGA) SPA beads (Perkin Elmer RPNQ0023) before equilibration with radioligand (2 nM 3H-ZM241385, 0.5 ug/well hA2A membrane, 50 ug/well YSI WGA, final concentration) and a concentration range of test compound (0.3% DMSO final concentration) in a final volume of 100 uL. Non-specific binding (NSB) was determined by 10 μM XAC. White, 384 well assay plates were used (Greiner #781207). Assay plates were incubated at room temperature until equilibrium (1.5 hours) before centrifugation and counting in a beta scintillation counter (TopCount NXT) with the measurement recorded as counts per minute (CPM). CPM was converted to percentage inhibition using the equation:

$$\left(\frac{(sample - NSB) - (TB - NSB)}{(TB - NSB)}\right) \times 100$$

Where total binding (TB) is binding in absence of competing compound.

The IC$_{50}$ obtained from the concentration response curves was converted to the inhibition constant (Ki) using the Cheng-Prusoff equation.

TABLE 11 h A$_{2A}$ Ki Values for example 1

| Example | h A$_{2A}$ Ki (nM) |
|---|---|
| 1 | 50 |

What is claimed is:

1. A metabolite of 5-bromo-2,6-di(1H-pyrazol-1-yl)pyrimindin-4-amine, which is compound:

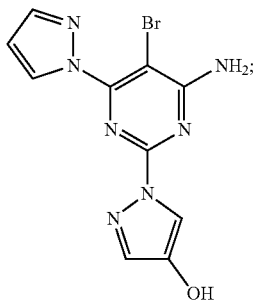 [SMILES: Nc1nc(-n2cc(O)cn2)nc(-n2cccn2)c1Br]

or a pharmaceutically acceptable salt thereof.

2. The compound 1-(4-amino-5-bromo-6-(1H-pyrazol-1-yl)-pyrimidin-2-yl)-1H-pyrazol-4-ol, in an isolated form.

3. A pharmaceutical composition comprising, 1-(4-amino-5-bromo-6-(1H-pyrazol-1-yl)-pyrimidin-2-yl)-1H-pyrazol-4-ol, or a pharmaceutically acceptable salt thereof, and at least one pharmaceutically acceptable excipient for simultaneous, concurrent, or sequential use.

4. A combination, comprising a therapeutically effective amount of 1-(4-amino-5-bromo-6-(1H-pyrazol-1-yl)-pyrimidin-2-yl)-1H-pyrazol-4-ol, or a pharmaceutically acceptable salt thereof and one or more immunotherapeutic agents.

5. A method of treating cancer, in a subject in need of such treatment, the method comprising: administering to a subject in need thereof, a therapeutically effective amount of 1-(4-amino-5-bromo-6-(1H-pyrazol-1-yl)-pyrimidin-2-yl)-1H-pyrazol-4-ol , or a pharmaceutically acceptable salt thereof; alone or in combination with one or more immunotherapeutic agents wherein the cancer is selected from a lung cancer, a melanoma, a renal cancer, a liver cancer, a myeloma, a prostate cancer, a breast cancer, a colorectal cancer, a pancreatic cancer, a head and neck cancer, anal cancer, gastro-esophageal cancer, thyroid cancer, cervical cancer, a lymphoproliferative disease or a hematological cancer, T-cell lymphoma, B-cell lymphoma, a non-Hogdkin lymphoma, or a leukemia.

6. A method of inhibiting adenosine A2a receptor in a subject, wherein the method comprises administering to the subject a therapeutically effective amount of the 1-(4-amino-5-bromo-6-(1H-pyrazol-1-yl)-pyrimidin-2-yl)-1H-pyrazol-4-ol according to claim 1; or administering a pharmaceutical composition according to claim 3 to a subject.

7. The method of claim 5, wherein the cancer is lung cancer.

8. The method of claim 5, wherein one or more immunotherapeutic agents are selected from the group consisting of anti-CTLA4 antibodies, anti-PD-1 antibodies and anti-PD-L1 antibodies.

9. The method of claim 5, wherein the immunotherapeutic agent is selected from the group consisting of: Ipilimumab, Tremelimumab, Nivolumab, Pembrolizumab, Pidilizumab (CT-011), AMP-224, AMP-514 (MEDI0680), MPDL3280A, MEDI4736, MSB0010718C, YW243.55.S70 and MDX-1105.

10. The method of claim 5, wherein the immunotherapeutic agents is an anti-PD-1 antibody.

11. The method, the use or the combination for use according to claim 10, wherein the anti-PD-1 antibody comprises:
(a) a heavy chain variable region (VH) comprising a VHCDR1 amino acid sequence of SEQ ID NO: 4, a VHCDR2 amino acid sequence of SEQ ID NO: 5, and a VHCDR3 amino acid sequence of SEQ ID NO: 3; and a light chain variable region (VL) comprising a VLCDR1 amino acid sequence of SEQ ID NO: 13, a VLCDR2 amino acid sequence of SEQ ID NO: 14, and a VLCDR3 amino acid sequence of SEQ ID NO: 15;
(b) a VH comprising a VHCDR1 amino acid sequence of SEQ ID NO: 1; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12;
(c) a VH comprising a VHCDR1 amino acid sequence of SEQ ID NO: 41, a VHCDR2 amino acid sequence of SEQ ID NO: 5, and a VHCDR3 amino acid sequence of SEQ ID NO: 3; and a VL comprising a VLCDR1 amino acid sequence of SEQ ID NO: 13, a VLCDR2 amino acid sequence of SEQ ID NO: 14, and a VLCDR3 amino acid sequence of SEQ ID NO: 15; or
(d) a VH comprising a VHCDR1 amino acid sequence of SEQ ID NO: 41; a VHCDR2 amino acid sequence of SEQ ID NO: 2; and a VHCDR3 amino acid sequence of SEQ ID NO: 3; and a VL comprising a VLCDR1 amino acid sequence of SEQ ID NO: 10, a VLCDR2 amino acid sequence of SEQ ID NO: 11, and a VLCDR3 amino acid sequence of SEQ ID NO: 12.

12. The method, according to claim 10, wherein the anti-PD-1 comprises a VH comprising the amino acid sequence of SEQ ID NO: 6 and a VL comprising the amino acid sequence of SEQ ID NO: 20.

13. The method, according to embodiment 10, wherein the anti-PD-1 antibody comprises a heavy chain comprising the amino acid sequence of SEQ ID NO: 8 and a light chain comprising the amino acid sequence of SEQ ID NO: 22.

14. The method, according to embodiment 10, wherein the anti-PD-1 antibody comprises a VH comprising the amino acid sequence of SEQ ID NO: 6 and a VL comprising the amino acid sequence of SEQ ID NO: 16.

15. The method, according to embodiment 10, wherein the anti-PD-1 antibody comprises a heavy chain comprising the amino acid sequence of SEQ ID NO: 8 and a light chain comprising the amino acid sequence of SEQ ID NO: 18.

16. The method, according to claim 10, wherein the anti-PD-1 antibody molecule is administered at a dose of about 300 mg once every three weeks.

17. The method, according to claim 10, wherein the anti-PD-1 antibody molecule is administered at a dose of about 400 mg once every four weeks.

18. The method of claim 5, wherein the immunotherapeutic agents is an anti-PD-L1 antibody.

19. The method, according to claim 18, wherein the anti PD-L1 antibody molecule comprises:
(a) a heavy chain variable region (VH) comprising a VHCDR1 amino acid sequence of SEQ ID NO: 47, a VHCDR2 amino acid sequence of SEQ ID NO: 48, and a VHCDR3 amino acid sequence of SEQ ID NO: 46; and a light chain variable region (VL) comprising a VLCDR1 amino acid sequence of SEQ ID NO: 52, a VLCDR2 amino acid sequence of SEQ ID NO: 53, and a VLCDR3 amino acid sequence of SEQ ID NO: 54;

(b) a VH comprising a VHCDR1 amino acid sequence of SEQ ID NO: 44; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51;

(c) a VH comprising a VHCDR1 amino acid sequence of SEQ ID NO: 63, a VHCDR2 amino acid sequence of SEQ ID NO: 48, and a VHCDR3 amino acid sequence of SEQ ID NO: 46; and a VL comprising a VLCDR1 amino acid sequence of SEQ ID NO: 52, a VLCDR2 amino acid sequence of SEQ ID NO: 53, and a VLCDR3 amino acid sequence of SEQ ID NO: 54; or (d) a VH comprising a VHCDR1 amino acid sequence of SEQ ID NO: 63; a VHCDR2 amino acid sequence of SEQ ID NO: 45; and a VHCDR3 amino acid sequence of SEQ ID NO: 46; and a VL comprising a VLCDR1 amino acid sequence of SEQ ID NO: 49, a VLCDR2 amino acid sequence of SEQ ID NO: 50, and a VLCDR3 amino acid sequence of SEQ ID NO: 51.

20. The method, according to claim 18, wherein the anti PD-L1 antibody molecule comprises a heavy chain variable domain comprising the amino acid sequence of SEQ ID NO: 55 and a light chain variable domain comprising the amino acid sequence of SEQ ID NO: 58.

21. The method, according to claim 8, wherein immunotherapeutic agent is administered together in a single composition or administered separately in two or more different compositions forms.

22. The method, according to claim 8, wherein the immunotherapeutic agent is administered concurrently with, prior to, or subsequent to, the compound: -(4-amino-5-bromo-6-(1H-pyrazol-1-yl)-pyrimidin-2-yl)-1H-pyrazol-4-ol.

23. The method according to claim 7, wherein the lung cancer is non-small cell lung cancer.

* * * * *